(12) United States Patent
Lum et al.

(10) Patent No.: US 7,780,631 B2
(45) Date of Patent: Aug. 24, 2010

(54) APPARATUS AND METHOD FOR PENETRATION WITH SHAFT HAVING A SENSOR FOR SENSING PENETRATION DEPTH

(75) Inventors: Paul Lum, Los Altos, CA (US); Hewlett E. Melton, Jr., Sunnyvale, CA (US); Tad Decataur Simons, Palo Alto, CA (US); Michael Greenstein, Los Altos, CA (US); Dominique M. Freeman, La Honda, CA (US)

(73) Assignee: Pelikan Technologies, Inc., Palo Alto, CA (US)

( * ) Notice: Subject to any disclaimer, the term of this patent is extended or adjusted under 35 U.S.C. 154(b) by 722 days.

(21) Appl. No.: 10/008,159

(22) Filed: Nov. 6, 2001

(65) Prior Publication Data
US 2002/0042594 A1     Apr. 11, 2002

Related U.S. Application Data

(63) Continuation of application No. 09/050,853, filed on Mar. 30, 1998, now Pat. No. 6,391,005.

(51) Int. Cl.
*A61M 5/00* (2006.01)
(52) U.S. Cl. ..................................... 604/117
(58) Field of Classification Search ............... 604/192, 604/194, 198, 117, 116, 264, 65–67, 272, 604/22, 46, 500, 503–505, 165.04, 187, 188, 604/131, 156, 134–136, 157; 600/382, 398, 600/399, 506, 347, 576, 583, 300, 554, 373, 600/546, 582, 568, 372, 573; 606/181, 182, 606/41, 10, 31, 1; 128/DIG. 12; 73/863, 73/864.4, 865.8; 83/61, 209; 607/122
See application file for complete search history.

(56) References Cited

U.S. PATENT DOCUMENTS

| | | | | |
|---|---|---|---|---|
| 2,714,890 | A | | 8/1955 | Vang ........................ 128/305 |
| 2,763,935 | A | * | 9/1956 | Whaley et al. ............... 33/511 |
| 3,086,288 | A | | 4/1963 | Balamuth et al. ............ 30/272 |
| 3,208,452 | A | | 9/1965 | Stern ......................... 128/315 |
| 3,358,689 | A | | 12/1967 | Higgins ..................... 128/329 |
| 3,494,358 | A | | 2/1970 | Grossenbacher ........... 128/218 |
| 3,626,929 | A | | 12/1971 | Sanz ......................... 128/2 R |

(Continued)

FOREIGN PATENT DOCUMENTS

DE          29824204          10/2000

(Continued)

*Primary Examiner*—Nicholas D Lucchesi
*Assistant Examiner*—Christopher D Koharski
(74) *Attorney, Agent, or Firm*—Paul Davis; Goodwin Procter LLP

(57) ABSTRACT

An apparatus having a shaft that can sense the depth of penetration, for penetrating into an object (the substrate). The substrate being penetrated has impedance that varies according to the depth under a surface of the substrate. The shaft has a tip for penetration and has conductive ends near to the tip of the shaft. A change of impedance of material of the object between the conductive ends can be sensed to provide information on the depth of penetration. A processor can be provided external to the object being penetrated by the shaft to gather and process the impedance information to determine whether the desired depth has been achieved.

15 Claims, 5 Drawing Sheets

U.S. PATENT DOCUMENTS

| | | | |
|---|---|---|---|
| 3,673,475 A | 6/1972 | Britton, Jr. ............... 318/122 |
| 3,742,954 A | 7/1973 | Strickland ............... 128/302 |
| 3,832,776 A | 9/1974 | Sawyer ............... 30/272 |
| 3,953,172 A | 4/1976 | Shapiro ............... 23/230 |
| 4,077,406 A | 3/1978 | Sandhage et al. ............... 128/217 |
| 4,154,228 A | 5/1979 | Feldstein et al. ............... 128/325 |
| 4,191,193 A * | 3/1980 | Seo ............... 600/488 |
| 4,203,446 A | 5/1980 | Höfert et al. ............... 128/329 |
| 4,223,674 A | 9/1980 | Fluent et al. ............... 128/217 |
| 4,224,125 A | 9/1980 | Nakamura ............... 204/195 B |
| 4,230,118 A | 10/1980 | Holman et al. ............... 128/314 |
| 4,299,230 A * | 11/1981 | Kubota ............... 600/300 |
| 4,340,669 A | 7/1982 | Bauer ............... 435/14 |
| 4,353,984 A | 10/1982 | Yamada ............... 435/14 |
| 4,356,826 A * | 11/1982 | Kubota ............... 600/300 |
| 4,360,016 A | 11/1982 | Sarrine ............... 128/763 |
| 4,391,905 A | 7/1983 | Bauer ............... 435/14 |
| 4,391,906 A | 7/1983 | Bauer ............... 435/14 |
| 4,414,975 A | 11/1983 | Ryder ............... 128/314 |
| 4,426,451 A | 1/1984 | Columbus ............... 436/518 |
| 4,426,884 A | 1/1984 | Polchaninoff ............... 73/172 |
| 4,449,529 A | 5/1984 | Burns et al. ............... 128/314 |
| 4,462,405 A | 7/1984 | Ehrlich ............... 128/329 |
| 4,469,110 A | 9/1984 | Slama ............... 128/770 |
| 4,517,978 A | 5/1985 | Levin ............... 128/314 |
| 4,518,384 A | 5/1985 | Tarello et al. ............... 604/61 |
| 4,535,773 A * | 8/1985 | Yoon ............... 606/185 |
| 4,539,988 A | 9/1985 | Shirley ............... 128/314 |
| 4,545,382 A | 10/1985 | Higgins ............... 128/635 |
| 4,553,541 A | 11/1985 | Burns ............... 128/314 |
| 4,577,630 A | 3/1986 | Nitzsche ............... 128/314 |
| 4,580,564 A | 4/1986 | Andersen ............... 502/8 |
| 4,580,565 A | 4/1986 | Cornell ............... 128/314 |
| 4,595,479 A | 6/1986 | Kimura ............... 204/294 |
| 4,608,997 A | 9/1986 | Conway ............... 128/763 |
| 4,615,340 A | 10/1986 | Cronenberg ............... 128/635 |
| 4,616,649 A | 10/1986 | Burns ............... 128/314 |
| 4,619,754 A | 10/1986 | Niki ............... 204/290 |
| 4,622,974 A | 11/1986 | Coleman ............... 128/634 |
| 4,624,253 A | 11/1986 | Burns ............... 128/314 |
| 4,627,445 A | 12/1986 | Garcia et al. ............... 128/770 |
| 4,637,393 A * | 1/1987 | Ray ............... 606/166 |
| 4,637,403 A | 1/1987 | Garcia et al. ............... 128/770 |
| 4,643,189 A | 2/1987 | Mintz ............... 128/314 |
| 4,648,408 A | 3/1987 | Hutcheson ............... 128/770 |
| 4,653,511 A | 3/1987 | Goch ............... 128/763 |
| 4,653,513 A | 3/1987 | Dombrowski ............... 128/765 |
| 4,674,503 A * | 6/1987 | Peyman et al. ............... 606/166 |
| 4,676,244 A | 6/1987 | Enstrom ............... 128/314 |
| 4,677,979 A | 7/1987 | Burns ............... 128/314 |
| 4,711,245 A | 12/1987 | Higgins ............... 128/635 |
| 4,712,548 A | 12/1987 | Enstrom ............... 128/314 |
| 4,715,374 A | 12/1987 | Maggio ............... 128/314 |
| 4,735,203 A | 4/1988 | Ryder ............... 128/314 |
| 4,750,489 A | 6/1988 | Berkman et al. ............... 128/314 |
| 4,757,022 A | 7/1988 | Shults et al. ............... 435/291 |
| 4,787,398 A | 11/1988 | Garcia et al. ............... 128/770 |
| 4,794,926 A | 1/1989 | Munsch et al. ............... 128/314 |
| RE32,922 E | 3/1989 | Levin ............... 128/314 |
| 4,814,142 A | 3/1989 | Gleisner ............... 422/56 |
| 4,814,661 A | 3/1989 | Ratzlaff ............... 310/328 |
| 4,820,010 A | 4/1989 | Scifres ............... 385/43 |
| 4,820,399 A | 4/1989 | Senda ............... 204/403 |
| 4,823,806 A | 4/1989 | Bajada ............... 128/744 |
| 4,824,639 A | 4/1989 | Hildenbrand ............... 422/56 |
| 4,825,711 A * | 5/1989 | Jensen et al. ............... 73/865.8 |
| 4,827,763 A | 5/1989 | Bourland ............... 73/172 |
| 4,830,959 A | 5/1989 | McNeil ............... 435/53 |
| 4,836,904 A | 6/1989 | Armstron ............... 204/294 |
| 4,844,095 A | 7/1989 | Chiodo ............... 128/314 |
| 4,850,973 A | 7/1989 | Jordan ............... 604/157 |
| 4,857,274 A | 8/1989 | Simon ............... 422/72 |
| 4,869,249 A | 9/1989 | Crossman ............... 128/314 |
| 4,869,265 A | 9/1989 | McEwen ............... 128/774 |
| 4,873,993 A | 10/1989 | Meserol ............... 128/780 |
| 4,882,013 A | 11/1989 | Turner ............... 204/1 |
| 4,883,068 A | 11/1989 | Dechow ............... 128/760 |
| 4,889,529 A | 12/1989 | Haindl ............... 604/274 |
| 4,892,097 A | 1/1990 | Ranalletta ............... 606/182 |
| 4,895,147 A | 1/1990 | Bodicky ............... 606/182 |
| 4,897,173 A | 1/1990 | Nankai ............... 204/403 |
| 4,900,424 A | 2/1990 | Birch ............... 204/409 |
| 4,911,794 A | 3/1990 | Parce ............... 204/1 T |
| 4,920,977 A | 5/1990 | Haynes ............... 128/770 |
| 4,924,879 A | 5/1990 | O'Brien ............... 128/770 |
| 4,940,468 A * | 7/1990 | Petillo ............... 606/170 |
| 4,945,045 A | 7/1990 | Forrest ............... 435/25 |
| 4,948,727 A | 8/1990 | Cass ............... 435/18 |
| 4,952,515 A | 8/1990 | Gleisner ............... 436/169 |
| 4,953,552 A | 9/1990 | DeMarzo ............... 128/635 |
| 4,966,671 A | 10/1990 | Nylander ............... 204/153.14 |
| 4,976,724 A | 12/1990 | Nieto ............... 606/182 |
| 4,983,178 A | 1/1991 | Schnell |
| 4,990,154 A | 2/1991 | Brown ............... 606/182 |
| 4,995,402 A | 2/1991 | Smith et al. ............... 128/771 |
| 5,010,772 A | 4/1991 | Bourland ............... 73/862.04 |
| 5,010,774 A | 4/1991 | Kikuo ............... 73/862.04 |
| 5,014,718 A | 5/1991 | Mitchen ............... 128/771 |
| 5,026,388 A | 6/1991 | Ingalz ............... 606/182 |
| 5,029,583 A | 7/1991 | Meserol et al. ............... 128/633 |
| 5,035,704 A | 7/1991 | Lambert et al. ............... 606/182 |
| 5,047,044 A | 9/1991 | Smith et al. ............... 606/182 |
| 5,054,499 A | 10/1991 | Swierczek ............... 128/770 |
| 5,059,789 A | 10/1991 | Salcudean ............... 250/206.1 |
| 5,060,174 A | 10/1991 | Gross ............... 702/139 |
| 5,070,886 A | 12/1991 | Mitchen ............... 128/771 |
| 5,074,872 A | 12/1991 | Brown ............... 606/182 |
| 5,089,112 A | 2/1992 | Skotheim ............... 204/403 |
| 5,092,842 A | 3/1992 | Bechtold ............... 604/135 |
| 5,097,810 A | 3/1992 | Fishman et al. ............... 128/743 |
| 5,100,427 A | 3/1992 | Crossman ............... 606/182 |
| 5,100,428 A | 3/1992 | Mumford ............... 606/182 |
| 5,104,380 A | 4/1992 | Holman ............... 604/117 |
| 5,104,619 A | 4/1992 | Castro ............... 422/56 |
| 5,108,564 A | 4/1992 | Szuminsky ............... 204/153.12 |
| 5,116,759 A | 5/1992 | Klainer ............... 435/288 |
| 5,120,420 A | 6/1992 | Nankai ............... 204/403 |
| 5,122,244 A | 6/1992 | Hoenes ............... 204/153 |
| 5,126,034 A | 6/1992 | Carter ............... 204/403 |
| 5,128,015 A | 7/1992 | Szuminsky ............... 204/403 |
| 5,128,171 A | 7/1992 | Gleisner ............... 427/2 |
| 5,133,730 A | 7/1992 | Biro ............... 606/182 |
| 5,139,685 A | 8/1992 | Castro ............... 210/767 |
| 5,141,868 A | 8/1992 | Shanks ............... 435/288 |
| 5,145,565 A | 9/1992 | Kater et al. ............... 204/153.1 |
| 5,152,775 A | 10/1992 | Ruppert ............... 606/182 |
| 5,156,611 A | 10/1992 | Haynes ............... 606/181 |
| 5,163,442 A | 11/1992 | Ono ............... 128/760 |
| 5,170,364 A | 12/1992 | Gross ............... 702/139 |
| D332,490 S | 1/1993 | Brown ............... D24/146 |
| 5,185,256 A | 2/1993 | Nankai ............... 435/174 |
| 5,187,100 A | 2/1993 | Matzinger ............... 436/16 |
| 5,188,118 A | 2/1993 | Terwilliger ............... 128/753 |
| 5,189,751 A | 3/1993 | Giuliani et al. ............... 15/22.1 |
| 5,192,415 A | 3/1993 | Yoshioka ............... 204/403 |
| 5,196,025 A | 3/1993 | Ranalletta ............... 606/182 |
| 5,201,324 A | 4/1993 | Swierczek ............... 128/770 |
| 5,205,920 A | 4/1993 | Oyama ............... 204/403 |
| 5,212,879 A | 5/1993 | Biro ............... 29/437 |
| 5,217,480 A | 6/1993 | Haber ............... 606/182 |
| 5,222,504 A | 6/1993 | Solomon ............... 128/744 |
| 5,229,282 A | 7/1993 | Yoshioka ............... 435/177 |
| 5,230,866 A | 7/1993 | Shartle ............... 422/103 |
| 5,231,993 A | 8/1993 | Haber et al. |

| | | | |
|---|---|---|---|
| 5,249,583 A * | 10/1993 | Mallaby ................. 600/567 |
| 5,250,066 A | 10/1993 | Lambert ................. 606/181 |
| 5,253,656 A | 10/1993 | Rincoe ................... 128/782 |
| 5,256,998 A | 10/1993 | Becker ................... 335/229 |
| 5,264,103 A | 11/1993 | Yoshioka ................ 204/403 |
| 5,264,105 A | 11/1993 | Gregg ................... 204/403 |
| 5,264,106 A | 11/1993 | McAleer ................. 204/403 |
| 5,266,179 A | 11/1993 | Nankai .................. 204/401 |
| D342,573 S | 12/1993 | Cerola ................... D24/147 |
| 5,272,087 A | 12/1993 | El Murr .................. 435/291 |
| 5,279,294 A | 1/1994 | Anderson et al. ........ 128/633 |
| 5,282,822 A | 2/1994 | Macors ................... 606/182 |
| 5,286,362 A | 2/1994 | Hoenes ................... 204/403 |
| 5,286,364 A | 2/1994 | Yacynych ................ 204/418 |
| 5,288,636 A | 2/1994 | Pollmann ................ 435/288 |
| 5,304,192 A | 4/1994 | Crouse ................... 606/181 |
| 5,304,193 A | 4/1994 | Zhadanov ................ 606/182 |
| 5,312,590 A | 5/1994 | Gunasingham ........... 422/56 |
| 5,314,441 A | 5/1994 | Cusack ................... 606/182 |
| 5,314,442 A | 5/1994 | Morita ................... 606/182 |
| 5,316,012 A | 5/1994 | Siegal ................... 128/744 |
| 5,318,583 A | 6/1994 | Rabenau et al. |
| 5,320,607 A | 6/1994 | Ishibashi ................. 604/115 |
| 5,320,808 A | 6/1994 | Holen et al. ............. 422/64 |
| 5,324,302 A | 6/1994 | Crouse ................... 606/181 |
| 5,324,303 A | 6/1994 | Strong ................... 606/181 |
| 5,332,479 A | 7/1994 | Uenoyama ............ 204/153.12 |
| 5,350,392 A | 9/1994 | Purcell ................... 606/182 |
| 5,354,287 A | 10/1994 | Wacks ................... 604/232 |
| 5,354,447 A | 10/1994 | Uenoyama .............. 204/403 |
| 5,356,420 A | 10/1994 | Czernecki ............... 606/182 |
| 5,360,410 A | 11/1994 | Wacks ................... 604/232 |
| 5,366,469 A | 11/1994 | Steg ..................... 606/182 |
| 5,366,470 A | 11/1994 | Ramel ................... 606/183 |
| 5,366,609 A | 11/1994 | White .................... 204/403 |
| 5,368,047 A | 11/1994 | Suzuki et al. ............ 128/765 |
| 5,375,397 A | 12/1994 | Ferrand ................... 54/66 |
| 5,378,628 A | 1/1995 | Gratzel ................... 435/288 |
| 5,382,346 A | 1/1995 | Uenoyama .............. 204/403 |
| 5,383,885 A | 1/1995 | Bland ................... 606/182 |
| 5,389,534 A | 2/1995 | Gentezkow ............. 435/180 |
| 5,393,903 A | 2/1995 | Graetzel ................. 556/137 |
| 5,395,387 A | 3/1995 | Burns |
| 5,397,334 A | 3/1995 | Schenk .................. 606/182 |
| 5,401,376 A | 3/1995 | Foos ..................... 204/415 |
| 5,402,798 A | 4/1995 | Swierczek ............... 128/770 |
| 5,407,545 A | 4/1995 | Hirose ................... 204/153.12 |
| 5,407,554 A | 4/1995 | Saurer ................... 204/403 |
| 5,407,818 A | 4/1995 | Gentezkow ............. 435/180 |
| 5,409,583 A | 4/1995 | Yoshioka ................ 204/153.12 |
| 5,410,059 A | 4/1995 | Fraser ................... 546/10 |
| 5,415,169 A | 5/1995 | Siczek et al. ............ 128/653.1 |
| 5,423,847 A | 6/1995 | Strong et al. ............ 606/182 |
| 5,436,161 A | 7/1995 | Bergstrom ............... 435/291 |
| 5,437,999 A | 8/1995 | Diebold ................. 435/288 |
| 5,443,701 A | 8/1995 | Willner ................. 204/153 |
| 5,445,920 A | 8/1995 | Saito ................... 430/311 |
| D362,719 S | 9/1995 | Kaplan ................. D24/147 |
| 5,454,828 A | 10/1995 | Schraga ................. 606/181 |
| 5,456,875 A | 10/1995 | Lambert ................. 264/328.1 |
| 5,460,182 A * | 10/1995 | Goodman et al. ......... 600/342 |
| 5,464,418 A | 11/1995 | Schraga ................. 606/182 |
| 5,471,102 A | 11/1995 | Becker .................. 310/50 |
| 5,472,427 A | 12/1995 | Rammler ................ 604/164 |
| 5,474,084 A | 12/1995 | Cunniff ................. 128/744 |
| 5,476,474 A | 12/1995 | Davis ................... 606/182 |
| 5,480,387 A | 1/1996 | Gabriel ................. 604/134 |
| 5,487,748 A | 1/1996 | Marshall ............... 606/182 |
| 5,496,453 A | 3/1996 | Uenoyama .............. 205/777.5 |
| 5,498,542 A | 3/1996 | Corey ................... 435/283.1 |
| 5,509,410 A | 4/1996 | Hill ..................... 128/637 |
| 5,510,266 A | 4/1996 | Bonner et al. |
| 5,510,366 A | 4/1996 | Bonner et al. ........... 436/43 |
| 5,512,159 A | 4/1996 | Yoshioka ................ 204/403 |
| 5,514,152 A | 5/1996 | Smith ................... 606/182 |
| 5,518,006 A | 5/1996 | Mawhirt ................ 128/770 |
| 5,524,636 A | 6/1996 | Sarvazyan .............. 128/774 |
| 5,525,511 A | 6/1996 | D'Costa ................. 435/287.9 |
| 5,527,333 A | 6/1996 | Nikkels ................. 606/182 |
| 5,527,334 A | 6/1996 | Kanner ................. 606/182 |
| 5,529,074 A | 6/1996 | Greenfield .............. 128/744 |
| 5,540,709 A | 7/1996 | Ramel .................. 606/183 |
| 5,543,326 A | 8/1996 | Heller .................. 435/287.9 |
| 5,545,174 A | 8/1996 | Schenk ................. 606/182 |
| 5,547,702 A | 8/1996 | Gleisner ................ 427/2.13 |
| 5,554,166 A | 9/1996 | Lange .................. 606/182 |
| 5,558,834 A | 9/1996 | Chu .................... 422/55 |
| 5,569,286 A | 10/1996 | Peckham ............... 606/181 |
| 5,569,287 A | 10/1996 | Tezuka ................. 606/182 |
| 5,571,132 A | 11/1996 | Mawhirt ................ 606/182 |
| 5,575,403 A | 11/1996 | Charlton et al. .......... 221/31 |
| 5,575,895 A | 11/1996 | Ikeda ................... 204/403 |
| 5,582,697 A | 12/1996 | Ikeda ................... 204/403 |
| 5,584,846 A | 12/1996 | Mawhirt ................ 606/181 |
| 5,593,852 A | 1/1997 | Heller .................. 435/14 |
| 5,609,749 A | 3/1997 | Yamauchi .............. 205/777.5 |
| 5,613,978 A | 3/1997 | Harding ................. 606/181 |
| 5,620,279 A | 4/1997 | Furusawa ............... 204/402 |
| 5,624,537 A | 4/1997 | Turner .................. 204/403 |
| D379,516 S | 5/1997 | Rutter .................. D24/146 |
| 5,628,764 A | 5/1997 | Schraga ................. 606/182 |
| 5,628,765 A | 5/1997 | Morita .................. 606/182 |
| 5,628,890 A | 5/1997 | Carter .................. 204/403 |
| 5,630,986 A | 5/1997 | Charlton et al. ........... 422/64 |
| 5,632,410 A | 5/1997 | Moulton et al. .......... 221/79 |
| 5,643,306 A | 7/1997 | Schraga ................. 606/182 |
| 5,645,555 A | 7/1997 | Davis .................. 606/182 |
| 5,650,062 A | 7/1997 | Ikeda ................... 205/778 |
| 5,653,863 A | 8/1997 | Genshaw ............... 205/777.5 |
| 5,657,760 A | 8/1997 | Ying et al. ............. 128/660.03 |
| 5,658,444 A | 8/1997 | Black .................. 204/415 |
| 5,662,127 A | 9/1997 | De Vaughn ............. 128/765 |
| 5,662,672 A | 9/1997 | Pambianchi ............. 606/181 |
| 5,680,872 A | 10/1997 | Sesekura ............... 128/760 |
| 5,682,884 A | 11/1997 | Hill .................... 128/637 |
| 5,683,562 A | 11/1997 | Schaffar ............... 204/403 |
| 5,695,947 A | 12/1997 | Guo .................... 435/11 |
| 5,700,695 A | 12/1997 | Yassinzadeh et al. ...... 436/180 |
| 5,705,045 A | 1/1998 | Park et al. .............. 204/403 |
| 5,708,247 A | 1/1998 | McAleer ................ 204/403 |
| 5,709,668 A | 1/1998 | Wacks .................. 604/232 |
| 5,710,011 A | 1/1998 | Forrow ................. 435/25 |
| 5,714,390 A | 2/1998 | Hallowitz et al. ........ 436/526 |
| 5,720,862 A | 2/1998 | Hamamoto ............. 204/403 |
| 5,720,924 A | 2/1998 | Eikmeier et al. ......... 422/102 |
| D392,391 S | 3/1998 | Douglas ................ D24/225 |
| 5,723,284 A | 3/1998 | Ye ...................... 435/4 |
| 5,727,548 A | 3/1998 | Hill .................... 128/637 |
| 5,730,753 A | 3/1998 | Morita .................. 606/181 |
| 5,733,300 A | 3/1998 | Pambianchi ............ 606/181 |
| D393,716 S | 4/1998 | Brenneman ............. D24/147 |
| D393,717 S | 4/1998 | Brenneman ............. D24/147 |
| 5,735,868 A * | 4/1998 | Lee .................... 606/189 |
| 5,738,244 A | 4/1998 | Charlton et al. .......... 221/26 |
| 5,741,634 A | 4/1998 | Nozoe .................. 435/4 |
| RE35,803 E | 5/1998 | Lange .................. 606/182 |
| 5,746,217 A | 5/1998 | Erickson ............... 128/760 |
| 5,755,733 A | 5/1998 | Morita .................. 606/182 |
| 5,758,643 A | 6/1998 | Wong et al. ............ 128/632 |
| 5,759,364 A | 6/1998 | Charlton ............... 204/403 |
| 5,762,770 A | 6/1998 | Pritchard ............... 204/403 |
| 5,770,369 A | 6/1998 | Meade .................. 435/6 |
| 5,772,586 A | 6/1998 | Heinonen .............. 600/300 |
| 5,772,677 A | 6/1998 | Mawhirt ................ 606/181 |
| 5,773,270 A | 6/1998 | D'Orazio .............. 435/177 |
| 5,776,157 A | 7/1998 | Thorne et al. ........... 606/182 |

| | | | |
|---|---|---|---|
| 5,776,719 A | 7/1998 | Douglas ................... 435/28 |
| 5,782,770 A | 7/1998 | Mooradian ............... 600/476 |
| 5,782,852 A | 7/1998 | Foggia ..................... 606/182 |
| 5,788,651 A | 8/1998 | Weilandt .................. 600/567 |
| 5,788,652 A | 8/1998 | Rahn ....................... 600/577 |
| 5,795,725 A | 8/1998 | Buechler .................. 435/7.1 |
| 5,795,774 A | 8/1998 | Matsumoto ............. 435/287.9 |
| 5,797,940 A | 8/1998 | Mawhirt ................... 606/167 |
| 5,797,942 A | 8/1998 | Schraga ................... 606/182 |
| 5,798,030 A | 8/1998 | Raguse .................... 204/403 |
| 5,798,031 A | 8/1998 | Charlton .................. 204/403 |
| 5,800,781 A | 9/1998 | Gavin et al. .............. 422/73 |
| 5,801,057 A | 9/1998 | Smart et al. .............. 436/68 |
| 5,810,199 A | 9/1998 | Charlton et al. ......... 221/31 |
| 8,800,781 | 9/1998 | Gavin ....................... 422/73 |
| 5,820,551 A | 10/1998 | Hill .......................... 600/347 |
| 5,823,973 A | 10/1998 | Racchini et al. ......... 600/573 |
| 5,824,491 A | 10/1998 | Priest ....................... 435/28 |
| 5,830,219 A | 11/1998 | Bird et al. ................. 606/130 |
| 5,840,020 A | 11/1998 | Heinonen ................. 600/309 |
| 5,840,171 A | 11/1998 | Birch ....................... 205/335 |
| 5,846,490 A | 12/1998 | Yokota et al. ............ 422/66 |
| 5,849,174 A | 12/1998 | Sanghera .................. 205/775 |
| 5,854,074 A | 12/1998 | Charlton et al. ......... 436/46 |
| D403,975 S | 1/1999 | Douglas ................... D10/81 |
| 5,855,801 A | 1/1999 | Lin et al. .................. 216/2 |
| 5,857,983 A | 1/1999 | Douglas ................... 600/538 |
| 5,860,922 A | 1/1999 | Gordon ..................... 600/431 |
| 5,863,800 A | 1/1999 | Eikmeier et al. ......... 436/48 |
| 5,866,353 A | 2/1999 | Berneth .................... 435/26 |
| 5,868,772 A | 2/1999 | LeVaughn ................ 606/181 |
| 5,869,972 A | 2/1999 | Birch ....................... 324/439 |
| 5,871,494 A | 2/1999 | Simons et al. ............ 606/181 |
| 5,872,713 A | 2/1999 | Douglas ................... 702/85 |
| 5,873,887 A | 2/1999 | King ........................ 606/182 |
| 5,876,957 A | 3/1999 | Douglas ................... 435/28 |
| 5,879,311 A | 3/1999 | Duchon et al. ........... 600/584 |
| 5,879,373 A | 3/1999 | Roeper ..................... 606/344 |
| 5,880,829 A | 3/1999 | Kauhaniemi et al. .... 356/246 |
| 5,882,494 A | 3/1999 | van Antwerp ............ 204/403 |
| 5,885,211 A | 3/1999 | Eppstein et al. .......... 600/309 |
| 5,891,053 A | 4/1999 | Sesekura .................. 600/583 |
| 5,893,848 A * | 4/1999 | Negus et al. .............. 606/41 |
| 5,900,130 A | 5/1999 | Benvegnu ................. 204/453 |
| 5,906,921 A | 5/1999 | Ikeda ....................... 435/25 |
| D411,619 S | 6/1999 | Duchon .................... D24/146 |
| 5,916,156 A | 6/1999 | Hildenbrand ............. 600/347 |
| 5,916,229 A | 6/1999 | Evans ....................... 606/171 |
| 5,916,230 A | 6/1999 | Brenneman ............... 606/172 |
| 5,921,963 A | 7/1999 | Erez ......................... 604/192 |
| 5,922,188 A | 7/1999 | Ikeda ....................... 204/777.5 |
| RE36,268 E | 8/1999 | Szuminsky ............... 205/777.5 |
| 5,935,075 A | 8/1999 | Casscells .................. 600/474 |
| 5,938,679 A | 8/1999 | Freeman et al. .......... 606/181 |
| 5,951,492 A | 9/1999 | Douglas ................... 600/583 |
| 5,951,582 A | 9/1999 | Thorne et al. ............ 606/182 |
| 5,951,836 A | 9/1999 | McAleer ................... 204/403 |
| 5,954,738 A | 9/1999 | LeVaughn ................ 606/181 |
| 5,958,199 A | 9/1999 | Miyamoto ................ 204/403 |
| 5,965,380 A | 10/1999 | Heller ...................... 435/14 |
| 5,968,063 A | 10/1999 | Chu et al. ................. 606/185 |
| 5,971,941 A | 10/1999 | Simons et al. ............ 600/573 |
| 5,972,199 A | 10/1999 | Heller ...................... 205/777.5 |
| 5,983,193 A | 11/1999 | Heinonen ................. 705/2 |
| 5,985,116 A | 11/1999 | Ikeda ....................... 204/403 |
| 5,993,400 A | 11/1999 | Rincoe ..................... 600/595 |
| 5,997,561 A | 12/1999 | Böcker et al. ............ 606/182 |
| 5,997,817 A | 12/1999 | Crismore .................. 422/58 |
| 5,997,818 A | 12/1999 | Hackner ................... 422/681 |
| 6,001,067 A | 12/1999 | Shults ...................... 600/584 |
| 6,020,110 A | 2/2000 | Williams .................. 430/315 |
| 6,022,324 A | 2/2000 | Skinner .................... 600/566 |
| 6,022,366 A | 2/2000 | Schraga ................... 606/181 |
| 6,027,459 A * | 2/2000 | Shain et al. .............. 600/573 |
| 6,030,399 A | 2/2000 | Ignotz ...................... 606/167 |
| 6,030,827 A | 2/2000 | Davis ....................... 435/287 |
| 6,033,421 A | 3/2000 | Theiss ...................... 606/186 |
| 6,033,866 A | 3/2000 | Guo ......................... 435/14 |
| 6,036,924 A | 3/2000 | Simons et al. ............ 422/100 |
| 6,048,352 A | 4/2000 | Douglas et al. .......... 606/181 |
| D424,696 S | 5/2000 | Ray ......................... D24/169 |
| 6,060,327 A | 5/2000 | Keen ........................ 436/518 |
| 6,063,039 A * | 5/2000 | Cunningham et al. ... 600/573 |
| 6,066,296 A | 5/2000 | Brady ...................... 422/63 |
| 6,067,463 A | 5/2000 | Jeng ........................ 600/336 |
| D426,638 S | 6/2000 | Ray ......................... D24/169 |
| 6,071,249 A * | 6/2000 | Cunningham et al. ... 600/578 |
| 6,071,250 A | 6/2000 | Douglas ................... 600/583 |
| 6,071,251 A * | 6/2000 | Cunningham et al. ... 600/584 |
| 6,071,294 A | 6/2000 | Simons et al. ............ 606/181 |
| 6,074,360 A | 6/2000 | Haar et al. ................ 604/57 |
| 6,077,408 A | 6/2000 | Miyamoto ................ 204/403 |
| 6,080,172 A | 6/2000 | Fujiwara .................. 606/166 |
| 6,083,710 A | 7/2000 | Heller ...................... 435/14 |
| 6,086,562 A | 7/2000 | Jacobsen .................. 604/156 |
| 6,093,156 A * | 7/2000 | Cunningham et al. ... 600/573 |
| 6,103,033 A | 8/2000 | Say .......................... 156/73.1 |
| 6,107,083 A | 8/2000 | Collins ..................... 435/288 |
| 6,117,630 A | 9/2000 | Reber et al. .............. 435/4 |
| 6,120,462 A | 9/2000 | Hibner et al. ............. 600/566 |
| 6,120,676 A | 9/2000 | Heller ...................... 205/777.5 |
| 6,121,009 A | 9/2000 | Heller ...................... 435/14 |
| 6,129,823 A | 10/2000 | Hughes .................... 204/403.01 |
| 6,132,449 A | 10/2000 | Lum et al. ................ 606/181 |
| 6,133,837 A | 10/2000 | Riley ....................... 340/573.1 |
| 6,134,461 A | 10/2000 | Say .......................... 600/345 |
| 6,136,013 A | 10/2000 | Marshall et al. .......... 606/167 |
| 6,139,562 A | 10/2000 | Mauze et al. ............. 606/171 |
| 6,143,164 A | 11/2000 | Heller et al. .............. 205/777.5 |
| 6,152,942 A | 11/2000 | Brenneman et al. ..... 606/181 |
| 6,153,069 A | 11/2000 | Pottgen .................... 204/403 |
| RE36,991 E | 12/2000 | Yamamoto ............... 204/403 |
| 6,155,992 A * | 12/2000 | Henning et al. .......... 600/583 |
| 6,156,051 A | 12/2000 | Schraga ................... 606/181 |
| 6,157,442 A | 12/2000 | Raskas ..................... 356/39 |
| 6,159,424 A | 12/2000 | Kauhaniemi et al. .... 422/63 |
| 6,162,611 A | 12/2000 | Heller ...................... 435/14 |
| 6,171,325 B1 | 1/2001 | Mauze et al. ............. 356/446 |
| 6,175,752 B1 | 1/2001 | Say .......................... 600/345 |
| 6,176,865 B1 | 1/2001 | Mauze et al. ............. 606/171 |
| 6,177,000 B1 | 1/2001 | Peterson .................. 205/777.5 |
| 6,183,489 B1 | 2/2001 | Douglas et al. .......... 606/181 |
| 6,190,612 B1 | 2/2001 | Berger ..................... 422/82.07 |
| 6,191,852 B1 | 2/2001 | Paffhausen ............... 356/244 |
| 6,192,891 B1 | 2/2001 | Gravel ..................... 128/920 |
| 6,193,673 B1 | 2/2001 | Viola et al. ............... 600/568 |
| 6,194,900 B1 | 2/2001 | Freeman .................. 324/321 |
| 6,197,257 B1 | 3/2001 | Raskas ..................... 422/82.05 |
| 6,203,504 B1 | 3/2001 | Latterell et al. .......... 600/576 |
| 6,206,841 B1 | 3/2001 | Cunningham et al. |
| 6,210,420 B1 | 4/2001 | Mauze et al. ............. 606/182 |
| 6,210,421 B1 | 4/2001 | Böcker et al. ............ 606/182 |
| 6,212,417 B1 | 4/2001 | Ikeda ....................... 204/403.14 |
| 6,214,804 B1 | 4/2001 | Felgner .................... 514/44 |
| 6,221,238 B1 | 4/2001 | Grundig ................... 205/777.5 |
| 6,225,078 B1 | 5/2001 | Ikeda ....................... 435/25 |
| 6,228,100 B1 | 5/2001 | Schraga ................... 606/183 |
| 6,230,501 B1 | 5/2001 | Bailey ...................... 62/51.1 |
| 6,231,531 B1 | 5/2001 | Lum et al. ................ 601/46 |
| 6,241,862 B1 | 6/2001 | McAleer .................. 204/403 |
| 6,245,060 B1 | 6/2001 | Loomis .................... 606/9 |
| 6,251,260 B1 | 6/2001 | Heller ...................... 205/777.5 |
| 6,254,831 B1 | 7/2001 | Barnard ................... 422/82.08 |
| 6,256,533 B1 | 7/2001 | Yuzhakov ................ 604/21 |
| 6,258,229 B1 | 7/2001 | Winarta ................... 204/403 |
| 6,258,254 B1 | 7/2001 | Miyamoto ............... 205/777.5 |

| Patent | Date | Inventor | Class |
|---|---|---|---|
| 6,261,241 B1 | 7/2001 | Burbank et al. | 600/564 |
| 6,261,245 B1 | 7/2001 | Kawai et al. | 600/576 |
| 6,268,161 B1 | 7/2001 | Han | 435/14 |
| 6,270,637 B1 | 8/2001 | Crismore | 204/403 |
| 6,272,359 B1 | 8/2001 | Kivela | 455/567 |
| 6,281,006 B1 | 8/2001 | Heller | 435/287.9 |
| 6,283,926 B1 | 9/2001 | Cunningham et al. | 600/573 |
| 6,283,982 B1 | 9/2001 | Levaughn | 606/172 |
| 6,284,478 B1 | 9/2001 | Heller | 435/14 |
| 6,285,448 B1 | 9/2001 | Kuenstner | 356/39 |
| 6,285,454 B1 | 9/2001 | Douglas et al. | 356/446 |
| 6,290,683 B1 | 9/2001 | Erez | 604/273 |
| 6,295,506 B1 | 9/2001 | Heinonen | 702/104 |
| 6,299,757 B1 | 10/2001 | Feldman | 205/775 |
| 6,302,855 B1 | 10/2001 | Lav | 600/584 |
| 6,306,104 B1 | 10/2001 | Cunningham et al. | 600/573 |
| 6,306,152 B1 | 10/2001 | Verdonk et al. | 606/182 |
| 6,306,347 B1 | 10/2001 | Mason | 422/58 |
| 6,309,535 B1 | 10/2001 | Williams | 205/777.5 |
| 6,312,612 B1 | 11/2001 | Sherman | 216/2 |
| 6,315,738 B1 | 11/2001 | Nishikawa et al. | 600/583 |
| 6,319,210 B1 | 11/2001 | Douglas et al. | 600/583 |
| 6,322,574 B1 | 11/2001 | Lloyd | 606/181 |
| 6,331,163 B1 | 12/2001 | Kaplan | 600/486 |
| 6,332,871 B1 | 12/2001 | Douglas et al. | 600/583 |
| 6,334,363 B1 | 1/2002 | Testud | 73/862 |
| 6,334,856 B1 | 1/2002 | Allen | 604/191 |
| 6,338,790 B1 | 1/2002 | Feldman | 205/777.5 |
| 6,350,273 B1 | 2/2002 | Minagawa | 606/186 |
| 6,350,451 B1 | 2/2002 | Horn | 424/184.1 |
| 6,352,514 B1 | 3/2002 | Douglas et al. | 600/583 |
| 6,352,523 B1 | 3/2002 | Brown | 604/207 |
| 6,353,753 B1 | 3/2002 | Flock | 600/473 |
| 6,364,889 B1 | 4/2002 | Kheiri et al. | 606/181 |
| 6,364,890 B1 | 4/2002 | Lum et al. | 606/181 |
| 6,375,627 B1 | 4/2002 | Mauze et al. | 600/584 |
| 6,379,301 B1 | 4/2002 | WOrthington | 600/309 |
| 6,379,317 B1 | 4/2002 | Kintzig et al. | 600/573 |
| 6,379,324 B1 | 4/2002 | Gartstein | 604/22 |
| 6,379,969 B1 | 4/2002 | Mauze et al. | 436/68 |
| 6,387,709 B1 | 5/2002 | Mason | 436/164 |
| 6,391,005 B1 | 5/2002 | Lum et al. | 604/117 |
| 6,399,394 B1 | 6/2002 | Dahm | 436/180 |
| 6,402,701 B1 | 6/2002 | Kaplan et al. | 600/567 |
| 6,402,704 B1 | 6/2002 | McMorrow | 600/576 |
| 6,409,740 B1 | 6/2002 | Kuhr et al. | 606/182 |
| 6,413,410 B1 | 7/2002 | Hodges | 205/775 |
| 6,413,411 B1 | 7/2002 | Pottgen | 205/777.5 |
| 6,421,633 B1 | 7/2002 | Heinonen | 703/11 |
| 6,428,664 B1 | 8/2002 | Bhullar | 204/403.03 |
| 6,436,256 B1 | 8/2002 | Williams | 204/403.03 |
| 6,436,721 B1 | 8/2002 | Kuo | 436/514 |
| 6,440,645 B1 | 8/2002 | Yon-Hin | 430/322 |
| 6,451,040 B1 | 9/2002 | Purcell | 606/181 |
| 6,458,258 B2 | 10/2002 | Taniike | 204/403 |
| 6,461,496 B1 | 10/2002 | Feldman et al. | 205/777.5 |
| 6,462,162 B2 | 10/2002 | van Antwerp | 528/77 |
| 6,471,903 B2 | 10/2002 | Sherman | 264/328.1 |
| 6,472,220 B1 | 10/2002 | Simons et al. | 436/63 |
| 6,475,436 B1 | 11/2002 | Schabbach | 422/64 |
| 6,475,750 B1 | 11/2002 | Han | 435/14 |
| 6,484,046 B1 | 11/2002 | Say | 600/345 |
| 6,485,439 B1 | 11/2002 | Roe et al. | 600/578 |
| 6,488,891 B2 | 12/2002 | Mason et al. | 422/58 |
| 6,491,709 B2 | 12/2002 | Sharma et al. | 606/181 |
| 6,497,845 B1 | 12/2002 | Sacherer | 422/104 |
| 6,501,404 B2 | 12/2002 | Walker | 341/143 |
| 6,503,210 B1 | 1/2003 | Hirao et al. | 600/576 |
| 6,503,231 B1 | 1/2003 | Prausnitz | 604/272 |
| 6,506,168 B1* | 1/2003 | Fathallah et al. | 600/578 |
| 6,506,575 B1 | 1/2003 | Knappe et al. | 435/25 |
| 6,508,785 B1 | 1/2003 | Eppstein | 604/113 |
| 6,514,270 B1 | 2/2003 | Schraga | 606/182 |
| 6,514,460 B1 | 2/2003 | Fendrock | 422/55 |
| 6,519,241 B1 | 2/2003 | Theimer | 370/338 |
| 6,520,326 B2 | 2/2003 | McIvor | 206/305 |
| 6,527,778 B2 | 3/2003 | Athanasiou | 606/80 |
| 6,530,892 B1 | 3/2003 | Kelly | |
| 6,530,937 B1 | 3/2003 | Schraga | 606/182 |
| 6,533,949 B1 | 3/2003 | Yeshurun | 216/11 |
| 6,537,242 B1 | 3/2003 | Palmer | 604/22 |
| 6,537,292 B1 | 3/2003 | Lee | 606/182 |
| 6,540,672 B1 | 4/2003 | Simonsen | 600/300 |
| 6,540,675 B2 | 4/2003 | Aceti | 600/309 |
| 6,540,762 B1 | 4/2003 | Bertling | 606/182 |
| 6,540,891 B1 | 4/2003 | Stewart | 204/403.14 |
| 6,547,954 B2 | 4/2003 | Ikeda | 205/777.5 |
| 6,549,796 B2 | 4/2003 | Sohrab | 600/345 |
| 6,551,494 B1 | 4/2003 | Feldman | 205/777.5 |
| 6,555,061 B1 | 4/2003 | Leong | 422/58 |
| 6,558,361 B1 | 5/2003 | Yeshurun | 604/272 |
| 6,558,402 B1 | 5/2003 | Chelak | 606/182 |
| 6,558,528 B1 | 5/2003 | Matzinger | 205/777.5 |
| 6,561,989 B2 | 5/2003 | Whitson | 600/573 |
| 6,565,808 B2 | 5/2003 | Hudak | 422/58 |
| 6,569,157 B1 | 5/2003 | Shain | 606/12 |
| 6,571,651 B1 | 6/2003 | Hodges | 73/864.72 |
| 6,572,566 B2 | 6/2003 | Effenhauser | 600/584 |
| 6,574,490 B2 | 6/2003 | Abbink | 600/316 |
| 6,576,101 B1 | 6/2003 | Heller | 204/403.14 |
| 6,576,416 B2 | 6/2003 | Haviland | 435/4 |
| 6,579,690 B1 | 6/2003 | Bonnecaze et al. | 435/14 |
| 6,587,705 B1 | 7/2003 | Kim | 600/347 |
| 6,589,260 B1 | 7/2003 | Schmelzeisen-R | 606/181 |
| 6,589,261 B1 | 7/2003 | Abulhaj | 606/181 |
| 6,591,125 B1 | 7/2003 | Buse | 600/347 |
| 6,592,745 B1 | 7/2003 | Feldman | 205/777.5 |
| 6,599,407 B2 | 7/2003 | Taniike | 204/403.1 |
| 6,599,693 B1 | 7/2003 | Webb | 435/4 |
| 6,602,205 B1 | 8/2003 | Erickson | 600/573 |
| 6,602,268 B2 | 8/2003 | Kuhr | 606/181 |
| 6,602,678 B2 | 8/2003 | Kwon | 435/14 |
| 6,607,658 B1 | 8/2003 | Heller | 205/777.5 |
| 6,616,616 B2 | 9/2003 | Fritz | 600/583 |
| 6,616,819 B1 | 9/2003 | Liamos | 204/403.02 |
| 6,618,934 B1 | 9/2003 | Feldman | 29/830 |
| 6,620,112 B2 | 9/2003 | Klitmose | 600/583 |
| 6,623,501 B2 | 9/2003 | Heller | 606/181 |
| 6,626,851 B2 | 9/2003 | Hirao | 600/576 |
| 6,635,222 B2 | 10/2003 | Kent | 422/22 |
| 6,641,533 B2 | 11/2003 | Causey | 600/300 |
| 6,645,368 B1 | 11/2003 | Beaty | 205/792 |
| 6,652,720 B1 | 11/2003 | Mansouri | 204/403.11 |
| 6,656,702 B1 | 12/2003 | Yugawa | 435/26 |
| 6,659,966 B2 | 12/2003 | Essenpreis | 600/583 |
| 6,660,018 B2 | 12/2003 | Lum | 606/181 |
| 6,671,527 B2 | 12/2003 | Petersson | 600/316 |
| 6,679,841 B2 | 1/2004 | Bojan | 600/309 |
| 6,679,852 B1 | 1/2004 | Schmelzeisen-redeker et al. | 600/583 |
| 6,706,000 B2 | 3/2004 | Perez | 600/583 |
| 6,706,159 B2 | 3/2004 | Moerman | 204/403.03 |
| 6,706,232 B2 | 3/2004 | Hasegawa | 264/403.09 |
| 6,713,660 B1 | 3/2004 | Roe | 604/361 |
| 6,719,887 B2 | 4/2004 | Hasegawa | 204/403.09 |
| 6,723,111 B2 | 4/2004 | Abulhaj | 606/181 |
| 6,723,371 B2 | 4/2004 | Chih-hui | 472/2.13 |
| 6,723,500 B2 | 4/2004 | Yu | 435/4 |
| 6,726,818 B2 | 4/2004 | Cui et al. | 204/403.01 |
| 6,733,493 B2 | 5/2004 | Gruzdev | 606/9 |
| 6,736,777 B2 | 5/2004 | Kim | 600/365 |
| 6,740,215 B1 | 5/2004 | Yamamoto | 204/403.14 |
| 6,743,211 B1 | 6/2004 | PraUSnitz | 604/239 |
| 6,749,792 B2 | 6/2004 | Olson | 264/328.1 |
| 6,751,491 B2 | 6/2004 | Lew | 600/345 |
| 6,752,817 B2 | 6/2004 | Flora | 606/181 |

| Patent No. | Date | Name | Class |
|---|---|---|---|
| 6,759,190 B2 | 7/2004 | Lin | 435/4 |
| 6,764,496 B2 | 7/2004 | Schraga | 606/182 |
| 6,764,581 B1 | 7/2004 | Forrow | 204/403 |
| 6,767,441 B1 | 7/2004 | Cai | 204/403.03 |
| 6,773,671 B1 | 8/2004 | Lewis | 422/58 |
| 6,776,888 B2 | 8/2004 | Yamamoto | 204/403.06 |
| 6,780,645 B2 | 8/2004 | Hayter | 436/8 |
| 6,780,647 B2 | 8/2004 | Fujiwara | 436/169 |
| 6,783,502 B2 | 8/2004 | Orloff | 600/583 |
| 6,783,537 B1 | 8/2004 | Kuhr | 606/182 |
| 6,784,274 B2 | 8/2004 | van Antwerp | 528/77 |
| 6,786,874 B2 | 9/2004 | Grace | 600/573 |
| 6,787,013 B2 | 9/2004 | Chang | 204/412 |
| 6,787,109 B2 | 9/2004 | Haar | 422/82.05 |
| 6,790,327 B2 | 9/2004 | Nankai | 204/403.1 |
| 6,790,599 B1 | 9/2004 | Madou | 430/320 |
| 6,792,791 B2 | 9/2004 | Sato | 73/1.02 |
| 6,793,632 B2 | 9/2004 | Sohrab | 600/573 |
| 6,793,633 B2 | 9/2004 | Douglas | 600/583 |
| 6,793,802 B2 | 9/2004 | Lee | 205/777.5 |
| 6,797,150 B2 | 9/2004 | Kermani | 205/777.5 |
| 6,800,488 B2 | 10/2004 | Khan | 436/166 |
| 6,801,041 B2 | 10/2004 | Karinka | 324/444 |
| 6,801,804 B2 | 10/2004 | Miller | 604/20 |
| 6,802,199 B2 | 10/2004 | Hilgers | 72/370.1 |
| 6,802,811 B1 | 10/2004 | Slepian | 600/309 |
| 6,802,957 B2 | 10/2004 | Jung | 205/777.5 |
| 6,805,780 B1 | 10/2004 | Ryu | 204/403.01 |
| 6,808,908 B2 | 10/2004 | Yao | 435/181 |
| 6,808,937 B2 | 10/2004 | Ligler | 436/518 |
| 6,809,807 B1 | 10/2004 | Erickson | 356/213 |
| 6,811,557 B2 | 11/2004 | Schraga | 606/182 |
| 6,811,659 B2 | 11/2004 | Vachon | 204/224 |
| 6,811,753 B2 | 11/2004 | Hirao | 422/101 |
| 6,811,792 B2 | 11/2004 | Roser | 424/423 |
| 6,812,031 B1 | 11/2004 | Carlsson | 436/52 |
| 6,814,843 B1 | 11/2004 | Bhullar | 204/403.1 |
| 6,814,844 B2 | 11/2004 | Bhullar | 204/403.1 |
| 6,814,845 B2 | 11/2004 | Wilson | 204/486 |
| 6,815,186 B2 | 11/2004 | Clark | 435/183 |
| 6,816,742 B2 | 11/2004 | Kim | 600/345 |
| 6,818,180 B2 | 11/2004 | Douglas | 422/58 |
| 6,821,483 B2 | 11/2004 | Phillips | 422/58 |
| 6,823,750 B2 | 11/2004 | Hodges | 73/864.72 |
| 6,825,047 B1 | 11/2004 | Woudenberg | 436/518 |
| 6,827,250 B2 | 12/2004 | Uhland | 228/110.1 |
| 6,827,829 B2 | 12/2004 | Kawanaka | 204/403.02 |
| 6,830,551 B1 | 12/2004 | Uchigaki | 600/584 |
| 6,830,668 B2 | 12/2004 | Musho | 204/400 |
| 6,830,669 B2 | 12/2004 | Miyazaki | 204/409 |
| 6,833,540 B2 | 12/2004 | MacKenzie | 250/214 |
| 6,835,184 B1 | 12/2004 | Sage | 604/46 |
| 6,835,553 B2 | 12/2004 | Han | 435/14 |
| 6,837,858 B2 * | 1/2005 | Cunningham et al. | 600/573 |
| 6,837,976 B2 | 1/2005 | Cai | 204/403.14 |
| 6,837,988 B2 | 1/2005 | Leong | 205/792 |
| 6,840,912 B2 | 1/2005 | Kloepfer | 600/583 |
| 6,841,052 B2 | 1/2005 | Musho | 204/401 |
| 6,843,254 B2 | 1/2005 | Tapper | 128/898 |
| 6,847,451 B2 | 1/2005 | Pugh | 356/436 |
| 6,849,052 B2 | 2/2005 | Uchigaki | 600/584 |
| 6,849,168 B2 | 2/2005 | Crumly | 204/416 |
| 6,849,216 B2 | 2/2005 | Rappin | 264/134 |
| 6,850,790 B2 | 2/2005 | Berner | 600/347 |
| 2001/0017269 A1 | 8/2001 | Heller | 205/777.5 |
| 2001/0027328 A1 | 10/2001 | Lum et al. | 606/186 |
| 2001/0031931 A1 | 10/2001 | Cunningham et al. | 600/573 |
| 2001/0054319 A1 | 12/2001 | Heller et al. | 73/849 |
| 2002/0002344 A1 | 1/2002 | Douglas et al. | 600/583 |
| 2002/0004196 A1 | 1/2002 | Whitson | 435/4 |
| 2002/0025469 A1 | 2/2002 | Heller | 429/43 |
| 2002/0029058 A1 | 3/2002 | Levaughn et al. | 606/181 |
| 2002/0040230 A1 | 4/2002 | Kuhr et al. | 606/181 |
| 2002/0042090 A1 | 4/2002 | Heller | 435/14 |
| 2002/0044890 A1 | 4/2002 | Black | 422/56 |
| 2002/0052618 A1 | 5/2002 | Haar et al. | 606/181 |
| 2002/0053523 A1 | 5/2002 | Liamos | 205/787 |
| 2002/0057993 A1 | 5/2002 | Maisey | 422/82.01 |
| 2002/0076349 A1 | 6/2002 | Aitken | 422/58 |
| 2002/0078091 A1 | 6/2002 | Vu et al. | 707/513 |
| 2002/0081588 A1 | 6/2002 | Lumley-Woodyear | 435/6 |
| 2002/0082543 A1 | 6/2002 | Park et al. | 604/21 |
| 2002/0084196 A1 | 7/2002 | Liamos | 205/792 |
| 2002/0087056 A1 | 7/2002 | Aceti et al. | |
| 2002/0092612 A1 | 7/2002 | Davies | 156/292 |
| 2002/0103499 A1 | 8/2002 | Perez et al. | 606/182 |
| 2002/0120216 A1 | 8/2002 | Fritz et al. | 600/583 |
| 2002/0130042 A1 | 9/2002 | Moerman | 204/403.01 |
| 2002/0136667 A1 | 9/2002 | Subramanian | 422/100 |
| 2002/0136863 A1 | 9/2002 | Subramanian et al. | 428/156 |
| 2002/0137998 A1 | 9/2002 | Smart et al. | 600/347 |
| 2002/0148739 A2 | 10/2002 | Liamos | 205/787 |
| 2002/0160520 A1 | 10/2002 | Orloff | 436/72 |
| 2002/0161289 A1 | 10/2002 | Hopkins, II et al. | 600/322 |
| 2002/0168290 A1 | 11/2002 | Yuzhakov | 422/56 |
| 2002/0169393 A1 * | 11/2002 | Cunningham et al. | 600/573 |
| 2002/0176984 A1 | 11/2002 | Smart | 428/336 |
| 2002/0177761 A1 | 11/2002 | Orloff et al. | 600/309 |
| 2002/0188224 A1 | 12/2002 | Roe et al. | |
| 2003/0018282 A1 | 1/2003 | Effenhauser et al. | 600/583 |
| 2003/0018300 A1 | 1/2003 | Duchon et al. | |
| 2003/0028126 A1 | 2/2003 | List | |
| 2003/0050573 A1 | 3/2003 | Kuhr et al. | |
| 2003/0050656 A1 | 3/2003 | Schraga | 606/182 |
| 2003/0060730 A1 | 3/2003 | Perez | 600/576 |
| 2003/0073089 A1 | 4/2003 | Mauze | 435/6 |
| 2003/0073229 A1 | 4/2003 | Greenstein | 435/287.2 |
| 2003/0073931 A1 | 4/2003 | Boecker et al. | 600/573 |
| 2003/0083685 A1 | 5/2003 | Freeman et al. | |
| 2003/0083686 A1 | 5/2003 | Freeman et al. | 606/181 |
| 2003/0088191 A1 | 5/2003 | Freeman et al. | 600/583 |
| 2003/0089730 A1 | 5/2003 | May, Sr. | 221/232 |
| 2003/0093010 A1 | 5/2003 | Essenpreis | |
| 2003/0100040 A1 | 5/2003 | Bonnecaze | 435/14 |
| 2003/0106810 A1 | 6/2003 | Douglas | 205/777.5 |
| 2003/0109777 A1 | 6/2003 | Kloepfer et al. | 600/367 |
| 2003/0111357 A1 | 6/2003 | Black | 205/775 |
| 2003/0113827 A1 | 6/2003 | Burkoth | 435/14 |
| 2003/0116447 A1 | 6/2003 | Sturridge | 205/777.5 |
| 2003/0135333 A1 | 7/2003 | Aceti et al. | 702/31 |
| 2003/0143113 A2 | 7/2003 | Yuzkhaov | 422/56 |
| 2003/0144608 A1 | 7/2003 | Kojima et al. | 600/583 |
| 2003/0144609 A1 | 7/2003 | Kennedy | |
| 2003/0146110 A1 | 8/2003 | Karinka | 205/777.5 |
| 2003/0149348 A1 | 8/2003 | Raskas | |
| 2003/0149377 A1 | 8/2003 | Erickson et al. | 600/573 |
| 2003/0153900 A1 | 8/2003 | Aceti et al. | 604/890.1 |
| 2003/0191415 A1 | 10/2003 | Moerman et al. | 600/584 |
| 2003/0195435 A1 | 10/2003 | Williams | 600/583 |
| 2003/0195540 A1 | 10/2003 | Moerman | 606/181 |
| 2003/0199744 A1 | 10/2003 | Buse et al. | 600/347 |
| 2003/0199789 A1 | 10/2003 | Boecker et al. | 600/575 |
| 2003/0199790 A1 | 10/2003 | Boecker | 600/576 |
| 2003/0199791 A1 | 10/2003 | Boecker | 600/576 |
| 2003/0199891 A1 | 10/2003 | Arganer | 606/181 |
| 2003/0199893 A1 | 10/2003 | Boecker | 606/181 |
| 2003/0199894 A1 | 10/2003 | Boecker | 606/181 |
| 2003/0199896 A1 | 10/2003 | Boecker | 606/181 |
| 2003/0199897 A1 | 10/2003 | Boecker | 606/181 |
| 2003/0199898 A1 | 10/2003 | Boecker | 606/181 |
| 2003/0199899 A1 | 10/2003 | Boecker | 606/181 |
| 2003/0199900 A1 | 10/2003 | Boecker | 606/181 |
| 2003/0199901 A1 | 10/2003 | Boecker | 606/181 |
| 2003/0199902 A1 | 10/2003 | Boecker | 606/181 |
| 2003/0199903 A1 | 10/2003 | Boecker | 606/181 |
| 2003/0199904 A1 | 10/2003 | Boecker | 606/181 |

| Pub. No. | Date | Inventor | Class |
|---|---|---|---|
| 2003/0199905 A1 | 10/2003 | Boecker | 606/181 |
| 2003/0199906 A1 | 10/2003 | Boecker | 606/181 |
| 2003/0199907 A1 | 10/2003 | Boecker | 606/181 |
| 2003/0199908 A1 | 10/2003 | Boecker | 606/181 |
| 2003/0199909 A1 | 10/2003 | Boecker | 606/181 |
| 2003/0199910 A1 | 10/2003 | Boecker | 606/181 |
| 2003/0199911 A1 | 10/2003 | Boecker | 606/181 |
| 2003/0199912 A1 | 10/2003 | Pugh | 606/182 |
| 2003/0201194 A1 | 10/2003 | Heller | 205/777.5 |
| 2003/0203352 A1 | 10/2003 | Haviland | 435/4 |
| 2003/0206828 A1 | 11/2003 | Bell | 422/44 |
| 2003/0208140 A1 | 11/2003 | Pugh | 600/584 |
| 2003/0212344 A1 | 11/2003 | Yuzhakov | 600/583 |
| 2003/0212345 A1 | 11/2003 | McAllister | 600/584 |
| 2003/0212346 A1 | 11/2003 | McAllister | 600/584 |
| 2003/0212347 A1 | 11/2003 | Sohrab | 600/584 |
| 2003/0212423 A1 | 11/2003 | Pugh | 606/181 |
| 2003/0212424 A1 | 11/2003 | Briggs | 606/181 |
| 2003/0216767 A1 | 11/2003 | List | 606/181 |
| 2003/0217918 A1 | 11/2003 | Davies | 204/403.14 |
| 2003/0220552 A1 | 11/2003 | Reghabi | 600/365 |
| 2003/0220663 A1 | 11/2003 | Fletcher | 606/182 |
| 2003/0223906 A1 | 12/2003 | McAllister | 422/58 |
| 2003/0225429 A1 | 12/2003 | Garthe | 606/182 |
| 2003/0225430 A1 | 12/2003 | Sebraga | 606/182 |
| 2003/0228637 A1 | 12/2003 | Wang | 435/7.9 |
| 2003/0232370 A1 | 12/2003 | Trifiro | 435/6 |
| 2003/0233055 A1 | 12/2003 | Erickson | 600/573 |
| 2003/0233112 A1 | 12/2003 | Alden et al. | 606/181 |
| 2003/0233113 A1 | 12/2003 | Alden et al. | 606/182 |
| 2004/0006285 A1 | 1/2004 | Douglas | 600/583 |
| 2004/0007585 A1 | 1/2004 | Griffith | 221/232 |
| 2004/0009100 A1 | 1/2004 | Simons | 422/102 |
| 2004/0010279 A1 | 1/2004 | Freeman | 606/182 |
| 2004/0015064 A1 | 1/2004 | Parsons | 600/347 |
| 2004/0019250 A1 | 1/2004 | Catelli | 600/1 |
| 2004/0026243 A1 | 2/2004 | Davies | 204/403.14 |
| 2004/0030353 A1 | 2/2004 | Schmelzeisen-R | 606/201 |
| 2004/0031682 A1 | 2/2004 | Wilsey | 204/403.1 |
| 2004/0034318 A1 | 2/2004 | Fritz | 604/19 |
| 2004/0038045 A1 | 2/2004 | Smart | 428/446 |
| 2004/0039303 A1 | 2/2004 | Wurster | 600/584 |
| 2004/0039342 A1 | 2/2004 | Eppstein | 604/200 |
| 2004/0039407 A1 | 2/2004 | Sehraga | 606/181 |
| 2004/0039408 A1 | 2/2004 | Abulhaj | 606/181 |
| 2004/0049220 A1 | 3/2004 | Boecker | 606/181 |
| 2004/0054267 A1 | 3/2004 | Feldman | 600/316 |
| 2004/0054898 A1 | 3/2004 | Heller | 205/777.5 |
| 2004/0059256 A1 | 3/2004 | Perez | 600/583 |
| 2004/0060818 A1 | 4/2004 | Feldman | 204/403.01 |
| 2004/0061841 A1 | 4/2004 | Black | 355/30 |
| 2004/0064068 A1 | 4/2004 | DeNuzzio | 600/583 |
| 2004/0092995 A1 | 5/2004 | Boecker | 606/181 |
| 2004/0096991 A1 | 5/2004 | Zhang | 436/518 |
| 2004/0098010 A1 | 5/2004 | Davison | 606/181 |
| 2004/0102803 A1 | 5/2004 | Boecker | 606/183 |
| 2004/0106858 A1 | 6/2004 | Say | 600/345 |
| 2004/0106859 A1 | 6/2004 | Say | 600/345 |
| 2004/0106860 A1 | 6/2004 | Say | 600/345 |
| 2004/0106904 A1 | 6/2004 | Gonnelli | 604/173 |
| 2004/0106941 A1 | 6/2004 | Roe | 606/181 |
| 2004/0115754 A1 | 6/2004 | Chang | 435/14 |
| 2004/0115831 A1 | 6/2004 | Meathrel | 436/514 |
| 2004/0116829 A1 | 6/2004 | Raney | 600/573 |
| 2004/0122339 A1 | 6/2004 | Roe | |
| 2004/0127818 A1 | 7/2004 | Roe | 600/583 |
| 2004/0127819 A1 | 7/2004 | Roe | 600/583 |
| 2004/0127928 A1 | 7/2004 | Whitson | 606/181 |
| 2004/0127929 A1 | 7/2004 | Roe | 606/181 |
| 2004/0132167 A1 | 7/2004 | Rule | 435/287.1 |
| 2004/0133125 A1 | 7/2004 | Miyashita | 600/573 |
| 2004/0133127 A1 | 7/2004 | Roe | 600/583 |
| 2004/0138541 A1 | 7/2004 | Ward | 600/345 |
| 2004/0138588 A1 | 7/2004 | Saikley | 600/583 |
| 2004/0138688 A1 | 7/2004 | Girand | 606/181 |
| 2004/0146958 A1 | 7/2004 | Bae | 435/14 |
| 2004/0154932 A1 | 8/2004 | Deng | 205/777.5 |
| 2004/0157017 A1 | 8/2004 | Mauze | 428/35.7 |
| 2004/0157149 A1 | 8/2004 | Hofmann | 430/131 |
| 2004/0157319 A1 | 8/2004 | Keen | 435/287.2 |
| 2004/0157338 A1 | 8/2004 | Burke | 436/147 |
| 2004/0157339 A1 | 8/2004 | Burke | 436/149 |
| 2004/0158137 A1 | 8/2004 | Eppstein | 600/347 |
| 2004/0158271 A1 | 8/2004 | Hamamoto | 606/181 |
| 2004/0161737 A1 | 8/2004 | Yang | 435/5 |
| 2004/0162473 A1 | 8/2004 | Sohrab | 600/345 |
| 2004/0162474 A1 | 8/2004 | Kiser | 600/345 |
| 2004/0162506 A1 | 8/2004 | Duchon | 600/583 |
| 2004/0162573 A1 | 8/2004 | Keheiri | 606/182 |
| 2004/0167383 A1 | 8/2004 | Kim | 600/365 |
| 2004/0171057 A1 | 9/2004 | Yang | 435/6 |
| 2004/0171968 A1 | 9/2004 | Katsuki | 600/583 |
| 2004/0172000 A1 | 9/2004 | Roe | 604/361 |
| 2004/0173472 A1 | 9/2004 | Jung | 205/777.5 |
| 2004/0173488 A1 | 9/2004 | Griffin | 206/363 |
| 2004/0176705 A1 | 9/2004 | Stevens | 600/584 |
| 2004/0176732 A1 | 9/2004 | Frazier | 604/345 |
| 2004/0178066 A1 | 9/2004 | Miyazaki | 204/403.01 |
| 2004/0178067 A1 | 9/2004 | Miyazaki | 204/403.1 |
| 2004/0178216 A1 | 9/2004 | Brickwood | 221/268 |
| 2004/0180379 A1 | 9/2004 | van Duyne | 435/7.1 |
| 2004/0182703 A1 | 9/2004 | Bell | 204/403.11 |
| 2004/0185568 A1 | 9/2004 | Matsumoto | 436/8 |
| 2004/0186359 A1 | 9/2004 | Beaudoin | 600/310 |
| 2004/0186394 A1 | 9/2004 | Roe | 600/598 |
| 2004/0186500 A1 | 9/2004 | Koilke | 606/181 |
| 2004/0193201 A1 | 9/2004 | Kim | 606/181 |
| 2004/0194302 A1 | 10/2004 | Bhullar | 29/847 |
| 2004/0197231 A1 | 10/2004 | Katsuki | 422/68.1 |
| 2004/0197821 A1 | 10/2004 | Bauer | 437/7.1 |
| 2004/0199062 A1 | 10/2004 | Petersson | 600/316 |
| 2004/0200720 A1 | 10/2004 | Musho | 204/403.01 |
| 2004/0200721 A1 | 10/2004 | Bhullar | 204/403.01 |
| 2004/0202576 A1 | 10/2004 | Aceti | 422/82.05 |
| 2004/0204662 A1 | 10/2004 | Perez | 600/583 |
| 2004/0206625 A1 | 10/2004 | Bhullar | 204/403.1 |
| 2004/0206636 A1 | 10/2004 | Hodges | 205/792 |
| 2004/0206658 A1 | 10/2004 | Hammerstedt | 206/524.1 |
| 2004/0209307 A1 | 10/2004 | Valkirs | 435/7.1 |
| 2004/0209350 A1 | 10/2004 | Sakata | 435/287.1 |
| 2004/0209354 A1 | 10/2004 | Mathies | 435/287.2 |
| 2004/0210279 A1 | 10/2004 | Gruzdev | 607/89 |
| 2004/0211666 A1 | 10/2004 | Pamidi | 204/403.01 |
| 2004/0214253 A1 | 10/2004 | Paek | 435/7.92 |
| 2004/0215224 A1 | 10/2004 | Sakata | 606/181 |
| 2004/0215225 A1 | 10/2004 | Nakayama | 606/182 |
| 2004/0216516 A1 | 11/2004 | Sato | 73/64.56 |
| 2004/0217019 A1 | 11/2004 | Cai | 205/792 |
| 2004/0219535 A1 | 11/2004 | Bell | 435/6 |
| 2004/0220456 A1 | 11/2004 | Eppstein | 600/309 |
| 2004/0220495 A1 | 11/2004 | Cahir | 600/562 |
| 2004/0220603 A1 | 11/2004 | Rutynowski | 606/181 |
| 2004/0222092 A1 | 11/2004 | Musho | 204/401 |
| 2004/0224369 A1 | 11/2004 | Cai | 435/7.7 |
| 2004/0225230 A1 | 11/2004 | Liamos | 600/583 |
| 2004/0225311 A1 | 11/2004 | Levaughn | 606/181 |
| 2004/0225312 A1 | 11/2004 | Orloff | 606/182 |
| 2004/0230216 A1 | 11/2004 | Levaughn | 606/181 |
| 2004/0231984 A1 | 11/2004 | Lauks | 204/416 |
| 2004/0232009 A1 | 11/2004 | Okuda | 205/789 |
| 2004/0236250 A1 | 11/2004 | Hodges | 600/583 |
| 2004/0236251 A1 | 11/2004 | Roe | 600/583 |
| 2004/0236268 A1 | 11/2004 | Mitragotri | 604/20 |
| 2004/0236362 A1 | 11/2004 | Schraga | 606/181 |
| 2004/0238357 A1 | 12/2004 | Bhullar | 204/400 |
| 2004/0238358 A1 | 12/2004 | Forrow | 204/403 |

| Publication No. | Date | Inventor | Class |
|---|---|---|---|
| 2004/0238359 A1 | 12/2004 | Ikeda | 204/403.1 |
| 2004/0241746 A1 | 12/2004 | Adlassnig | 435/7.1 |
| 2004/0242977 A1 | 12/2004 | Dosmann | 600/315 |
| 2004/0243164 A1 | 12/2004 | D'Agostino | 606/181 |
| 2004/0243165 A1 | 12/2004 | Koike | 606/181 |
| 2004/0245101 A1 | 12/2004 | Willner | 204/403 |
| 2004/0248282 A1 | 12/2004 | Sobha | 435/287.2 |
| 2004/0248312 A1 | 12/2004 | Vreeke | 436/95 |
| 2004/0249310 A1 | 12/2004 | Shartle | 600/583 |
| 2004/0249311 A1 | 12/2004 | Haar | 600/584 |
| 2004/0249405 A1 | 12/2004 | Watanabe | 606/181 |
| 2004/0249406 A1 | 12/2004 | Griffin | 606/182 |
| 2004/0251131 A1 | 12/2004 | Ueno | 204/403 |
| 2004/0253634 A1 | 12/2004 | Wang | 435/7.1 |
| 2004/0254434 A1 | 12/2004 | Goodnow | 600/365 |
| 2004/0254599 A1 | 12/2004 | Lipoma | 606/181 |
| 2004/0256228 A1 | 12/2004 | Huang | 204/434 |
| 2004/0256248 A1 | 12/2004 | Burka | 205/792 |
| 2004/0256685 A1 | 12/2004 | Chou | 257/414 |
| 2004/0258564 A1 | 12/2004 | Charlton | 422/58 |
| 2004/0260204 A1 | 12/2004 | Boecker | 600/584 |
| 2004/0260324 A1 | 12/2004 | Fukuzawa | 606/181 |
| 2004/0260325 A1 | 12/2004 | Kuhr | 606/181 |
| 2004/0260326 A1 | 12/2004 | Lipoma | 606/182 |
| 2004/0260511 A1 | 12/2004 | Burke | 702/182 |
| 2004/0267105 A1 | 12/2004 | Monfre | 600/344 |
| 2004/0267160 A9 | 12/2004 | Perez | 600/583 |
| 2004/0267229 A1 | 12/2004 | Moerman | 604/500 |
| 2004/0267299 A1 | 12/2004 | Kuriger | 606/181 |
| 2004/0267309 A1 | 12/2004 | Mace | 606/182 |
| 2005/0000806 A1 | 1/2005 | Hsieh | 203/403.1 |
| 2005/0000807 A1 | 1/2005 | Wang | 204/403.81 |
| 2005/0000808 A1 | 1/2005 | Cui | 203/403.14 |
| 2005/0003470 A1 | 1/2005 | Nelson | 435/14 |
| 2005/0004494 A1 | 1/2005 | Perez | 600/583 |
| 2005/0008537 A1 | 1/2005 | Mosolu | 422/56 |
| 2005/0008851 A1 | 1/2005 | Ezoe | 428/336 |
| 2005/0009191 A1 | 1/2005 | Swenson | 436/43 |
| 2005/0010090 A1 | 1/2005 | Acosta | 600/316 |
| 2005/0010093 A1 | 1/2005 | Ford | 600/345 |
| 2005/0010134 A1 | 1/2005 | Douglas | 600/573 |
| 2005/0010137 A1 | 1/2005 | Hodges | 600/583 |
| 2005/0010198 A1 | 1/2005 | Marchitto | 606/9 |
| 2005/0011759 A1 | 1/2005 | Moerman | 204/403.03 |
| 2005/0013731 A1 | 1/2005 | Burke | 422/56 |
| 2005/0014997 A1 | 1/2005 | Ruchti | 600/310 |
| 2005/0015020 A1 | 1/2005 | Levaughn | 600/583 |
| 2005/0016844 A1 | 1/2005 | Burke | 204/403.1 |
| 2005/0019212 A1 | 1/2005 | Bhullar | 422/56 |
| 2005/0019219 A1 | 1/2005 | Oshiman | 422/82.12 |
| 2005/0019805 A1 | 1/2005 | Groll | 435/6 |
| 2005/0019945 A1 | 1/2005 | Groll | 436/169 |
| 2005/0019953 A1 | 1/2005 | Groll | 436/514 |
| 2005/0021066 A1 | 1/2005 | Kuhr | 606/181 |

FOREIGN PATENT DOCUMENTS

| | | |
|---|---|---|
| DE | 10032042 | 1/2002 |
| DE | 10057832 | 2/2002 |
| DE | 10142232 | 3/2003 |
| EP | 0289 269 | 11/1988 |
| EP | 0320109 | 6/1989 |
| EP | 0170375 | 5/1990 |
| EP | 0136362 | 12/1990 |
| EP | 0453283 | 10/1991 |
| EP | 0374355 | 6/1993 |
| EP | 0351891 | 9/1993 |
| EP | 0593096 | 4/1994 |
| EP | 0415388 | 5/1995 |
| EP | 0505494 | 7/1995 |
| EP | 0359831 | 8/1995 |
| EP | 0471986 | 10/1995 |
| EP | 0368474 | 12/1995 |
| EP | 0461601 | 12/1995 |
| EP | 0429076 | 1/1996 |
| EP | 0552223 | 7/1996 |
| EP | 0735363 | 10/1996 |
| EP | 0505504 | 3/1997 |
| EP | 0406304 | 8/1997 |
| EP | 0537761 | 8/1997 |
| EP | 0795601 | 9/1997 |
| EP | 0562370 | 11/1997 |
| EP | 0415393 | 12/1997 |
| EP | 0560336 | 5/1998 |
| EP | 0878 708 | 11/1998 |
| EP | 0505475 | 3/1999 |
| EP | 0901018 | 3/1999 |
| EP | 0470649 | 6/1999 |
| EP | 0847447 | 11/1999 |
| EP | 0964059 | 12/1999 |
| EP | 0969097 | 1/2000 |
| EP | 1021950 | 7/2000 |
| EP | 0894869 | 2/2001 |
| EP | 1074832 | 2/2001 |
| EP | 1093854 | 4/2001 |
| EP | 1101443 | 5/2001 |
| EP | 1114995 | 7/2001 |
| EP | 0736607 | 8/2001 |
| EP | 0730037 | 12/2001 |
| EP | 0636879 | 1/2002 |
| EP | 0851224 | 3/2002 |
| EP | 0856586 | 5/2002 |
| EP | 0817809 | 7/2002 |
| EP | 0872728 | 7/2002 |
| EP | 0795748 | 8/2002 |
| EP | 0685737 | 9/2002 |
| EP | 0880692 | 1/2004 |
| EP | 1246688 | 5/2004 |
| EP | 1790288 | 5/2007 |
| EP | 2039294 | 3/2009 |
| GB | 2168815 | 6/1986 |
| GB | 2335860 A | 10/1999 |
| GB | 2335990 A | 10/1999 |
| JP | HEI 4-194660 | 7/1992 |
| JP | 9-276235 | 10/1997 |
| JP | 2000-116768 | 4/2000 |
| WO | WO80/01389 | 7/1980 |
| WO | WO85/04089 | 9/1985 |
| WO | WO86/07632 | 12/1985 |
| WO | WO91/09139 | 6/1991 |
| WO | WO 93/02720 | 2/1993 |
| WO | WO93/02720 | 2/1993 |
| WO | WO93/06979 | 4/1993 |
| WO | WO93/12726 | 7/1993 |
| WO | WO 93/12726 | 7/1993 |
| WO | WO93/25898 | 12/1993 |
| WO | WO94/27140 | 11/1994 |
| WO | WO94/29703 | 12/1994 |
| WO | WO94/29704 | 12/1994 |
| WO | WO94/29731 | 12/1994 |
| WO | WO95/00662 | 1/1995 |
| WO | WO95/10223 | 4/1995 |
| WO | WO95/22597 | 8/1995 |
| WO | WO96/30431 | 10/1996 |
| WO | WO97/02359 | 1/1997 |
| WO | WO97/02487 | 1/1997 |
| WO | WO 97/11883 | 4/1997 |
| WO | WO97/18464 | 5/1997 |
| WO | WO97/30344 | 8/1997 |
| WO | WO97/42882 | 11/1997 |
| WO | WO97/42888 | 11/1997 |
| WO | WO97/45720 | 12/1997 |
| WO | WO98/03431 | 1/1998 |
| WO | WO98/19159 | 5/1998 |
| WO | WO98/20332 | 5/1998 |
| WO | WO98/20348 | 5/1998 |

| | | | | | | |
|---|---|---|---|---|---|---|
| WO | WO98/24366 | 6/1998 | | WO | WO 02/18940 | 3/2002 |
| WO | WO 98/024373 | 6/1998 | | WO | WO 02/32559 | 4/2002 |
| WO | WO98/35225 | 8/1998 | | WO | WO 02/41779 | 5/2002 |
| WO | WO99/03584 | 1/1999 | | WO | WO 02/44948 | 6/2002 |
| WO | WO99/05966 | 2/1999 | | WO | WO 02/056769 A1 | 7/2002 |
| WO | WO 99/13100 | 3/1999 | | WO | WO 02/059734 | 8/2002 |
| WO | WO 99/19507 | 4/1999 | | WO | WO 02/069791 | 9/2002 |
| WO | WO 99/19717 | 4/1999 | | WO | WO 02/077638 | 10/2002 |
| WO | WO 99/27852 | 6/1999 | | WO | WO 02/100251 | 12/2002 |
| WO | WO 99/62576 | 12/1999 | | WO | WO 02/100252 | 12/2002 |
| WO | WO 99/64580 | 12/1999 | | WO | WO 02/100253 | 12/2002 |
| WO | WO 00/09184 | 2/2000 | | WO | WO 02/100254 | 12/2002 |
| WO | WO 00/30186 | 5/2000 | | WO | WO 02/100460 | 12/2002 |
| WO | WO 00/39914 | 7/2000 | | WO | WO 02/100461 | 12/2002 |
| WO | WO 00/44084 | 7/2000 | | WO | WO 02/101343 | 12/2002 |
| WO | WO 00/50771 | 8/2000 | | WO | WO 02/101359 | 12/2002 |
| WO | WO 00/60340 | 10/2000 | | WO | WO 03/000321 | 1/2003 |
| WO | WO 00/64022 | 10/2000 | | WO | WO 03/023389 | 3/2003 |
| WO | WO 00/67245 | 11/2000 | | WO | WO 03/042691 | 5/2003 |
| WO | WO 00/67268 | 11/2000 | | WO | WO 03/045557 | 6/2003 |
| WO | WO 01/00090 | 1/2001 | | WO | WO 03/046542 | 6/2003 |
| WO | WO 01/00090 A1 | 1/2001 | | WO | WO 03/049609 | 6/2003 |
| WO | WO 01/75433 | 3/2001 | | WO | WO 03/050534 | 6/2003 |
| WO | WO 01/23885 | 4/2001 | | WO | WO 03/066128 | 8/2003 |
| WO | WO 01/25775 | 4/2001 | | WO | WO 03/070099 | 8/2003 |
| WO | WO 01/26813 | 4/2001 | | WO | WO 03/071940 | 9/2003 |
| WO | WO 01/33216 | 5/2001 | | WO | WO 03/082091 A2 | 10/2003 |
| WO | WO 01/34029 | 5/2001 | | WO | WO 03/088851 A1 | 10/2003 |
| WO | WO 01/36955 | 5/2001 | | WO | WO 2004/008130 | 1/2004 |
| WO | WO 01/40788 | 7/2001 | | WO | WO 2004/026130 | 4/2004 |
| WO | WO 01/57510 | 8/2001 | | WO | WO 2004/041082 | 5/2004 |
| WO | WO 01/64105 | 9/2001 | | WO | WO 2004/054455 | 7/2004 |
| WO | WO 01/66010 | 9/2001 | | WO | WO 2004/060174 | 7/2004 |
| WO | WO 01/66010 A1 | 9/2001 | | WO | WO 2004/060446 | 7/2004 |
| WO | WO 01/72225 | 10/2001 | | WO | WO 2004/091693 | 10/2004 |
| WO | WO 01/73124 | 10/2001 | | WO | WO 2004/107964 | 12/2004 |
| WO | WO 01/73395 | 10/2001 | | WO | WO 2004/107975 | 12/2004 |
| WO | WO 01/89691 | 11/2001 | | WO | WO 2004/112602 | 12/2004 |
| WO | WO 02/00101 | 1/2002 | | WO | WO 2004/112612 | 12/2004 |
| WO | WO 02/02796 | 1/2002 | | WO | WO 2005/001418 | 1/2005 |
| WO | WO 02/08750 | 1/2002 | | WO | WO 2005/104948 | 11/2005 |
| WO | WO 02/08753 | 1/2002 | | | | |
| WO | WO 02/08950 | 1/2002 | | | | |

\* cited by examiner

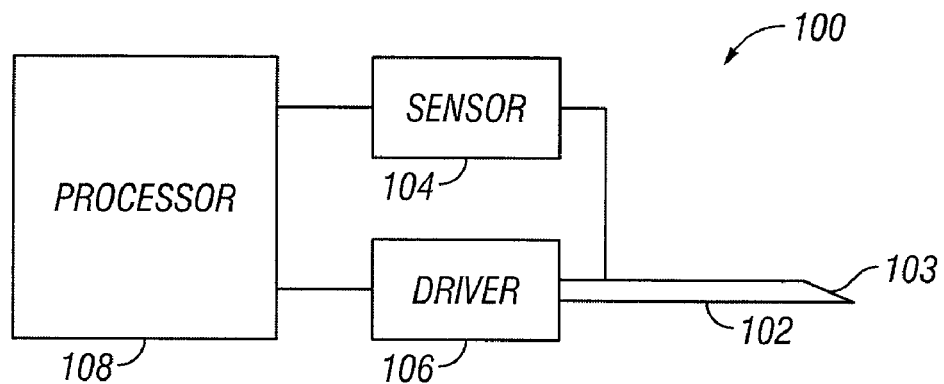
FIG. 1
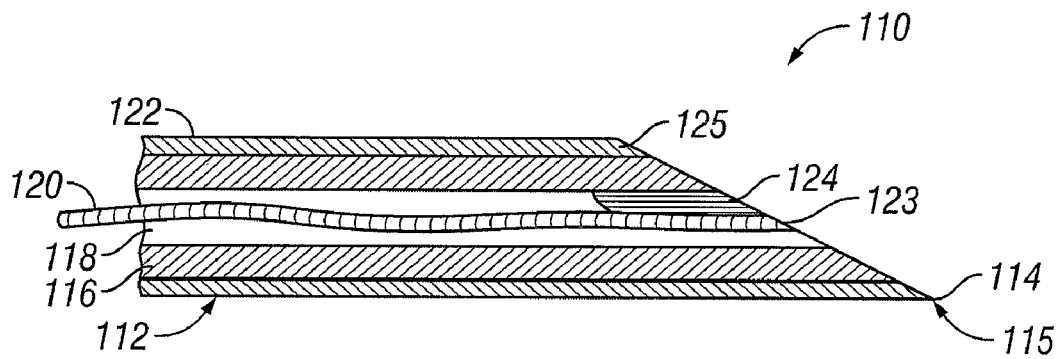
FIG. 2A
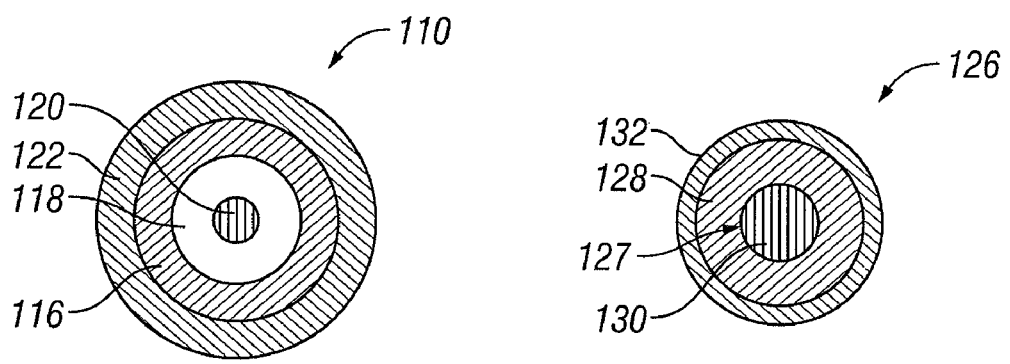
FIG. 2B  FIG. 3

APPARATUS AND METHOD FOR PENETRATION WITH SHAFT HAVING A SENSOR FOR SENSING PENETRATION DEPTH

FIELD OF THE INVENTION

This application is a continuation of U.S. patent application Ser. No. 09/050,853 entitled "Apparatus and Method for Penetration with Shaft having a Sensor for Sensing Penetration Depth", filed Mar. 30, 1998, now U.S. Pat. No. 6,391,005 which is incorporated herein by reference.

BACKGROUND

When inserting a long structure into an object, such as a needle into the tissue of a patient, it is often necessary to know how deep the penetration is. Penetration past the required depth for a desired result wastes effort and causes undue discomfort to the patient. Often the information is needed in a short time because further penetration may cause unnecessary damage to the object and it is desirable to stop the penetration once a predetermined depth is reached. For example, the analysis and quantification of blood components is an important diagnostic tool for better understanding the physical condition of a patient and blood samples need to be obtained by inflicting a wound by a needle or lancet. Inserting the needle or lancet to a depth deeper than necessary produces excessive pain and trauma to the skin tissue. In patients such as diabetics, who have to sample blood often, any excessive pain or tissue trauma is a disincentive to comply with the blood sampling routine.

The skin is consisted of two layers—the epidermis and the dermis. The capillary structures connected to the arterial and venous vascular beds rise vertically and are located in the dermis layer. The neural sensors such as Meissner's corpuscles and free nerve endings are also located in the dermis. Layers of subcutaneous tissues lie below the dermis. The supply arterial and venous capillaries are located laterally in this tissue bed. There is also adipose tissue interleaved with afferent and efferent nerve fibers along with their associated sensors interwoven within the vascular bed. The thicknesses of these tissue layers differ from individual to individual. Currently, commercially available needle or lancet for puncturing skin have preset penetration depth based on experimental data from lancing, Thus, there is no certainty that the optimal depth of penetration is reached every time such a needle or lancet is used. To avoid unsuccessful blood sampling due to inadequate depth, a patient often overpenetrates the skin, causing unnecessary pain.

What is needed is a needle or lancet for sampling blood that can be used for inserting to the optimal depth without over or under penetration. Similarly, there is a need in other penetration applications for inserting a long shaft into an object without over or under penetration.

SUMMARY

In the present invention, the depth of penetration of an elongated structure into an object is determined by an impedance sensor that senses the impedance of the material penetrated by the elongated structure at the tip of the elongated structure.

In one aspect, the present invention provides an apparatus having a shaft for penetration into an object which has impedance that varies according to the depth under a surface of the object. The apparatus contains a shaft that includes a shaft body having a tip for penetration and two conductive ends near the tip. The two conductive ends are near the tip such that a change of impedance of the material of the object sensed between the conductive ends will provide information on whether the desired depth of penetration has been reached.

This invention is especially applicable in obtaining blood from a patient by puncturing the skin because a shaft of the present invention takes advantage of the electrical impedance differences between deeper layers of skin tissue relative to the more shallow upper layer. The impedance can be monitored by, for example, a metallic needle that pierces the layers of skin tissue. When the needle initially penetrates into the outer epidermis and dermis layers of the skin, an initial high impedance is seen. A decline in the impedance is observed as the needle approaches the adipose layer.

Using the apparatus, including the shaft of the present invention, optimal penetration into an object that has electrical impedance which varies with penetration depth can be achieved. In the case of obtaining blood from a patient by inserting a needle into the skin, this can minimize the trauma and pain of overpenetration, as well as avoid the frustration and pain of unsuccessful blood sampling because of inadequate penetration. Such reduction of discomfort and tissue damage can significantly improve the compliance of patients with a blood sampling routine, for example.

BRIEF DESCRIPTION OF THE DRAWINGS

The following figures are included to better illustrate the embodiments of the apparatus and technique of the present invention. In these figures, like numerals represent like features in the several views.

FIG. 1 shows an embodiment of an apparatus of the present invention.

FIGS. 2A and 2B show an embodiment of a shaft of the present invention.

FIG. 3 shows another embodiment of a shaft of the present invention.

DETAILED DESCRIPTION OF THE INVENTION

Figure 4:
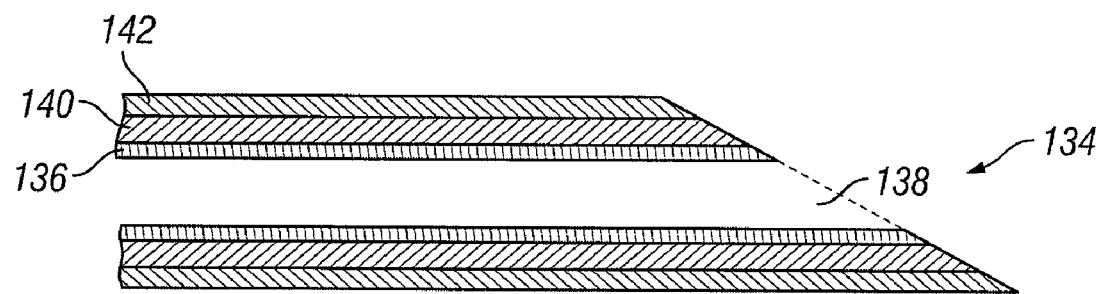
FIG. 4 shows yet another embodiment of a shaft of the present invention.

In one aspect, the present invention provides a technique for sensing the depth of penetration when inserting a shaft into a body. As used herein, the term "shaft" refers to an object with a generally elongated body with a tip for penetrating the body of interest. The body of the shaft, depending on the application, can be rigid or somewhat flexible. Preferably, the tip has a relative sharp point or beveled lancet to facilitate penetration. The point is adequate sharp such that the shaft can be pushed into the body without the need for passing along a preexisting hole. The body of the shaft can have a cross section that is round or non-round (e.g., having a rectangular cross section). As an example, a needle-sized shaft suitable for hypodermic insertion is described in the following embodiments. It is to be understood that other non-hypodermic shafts, including shafts for non-medical purposes, can be made and used according to the present invention.

Needles and Lancets

FIG. 1 shows an embodiment of an apparatus for driving a shaft for penetrating skin according to the present invention. In FIG. 1, the apparatus 100 includes a shaft 102 (e.g., a needle or lancet) with conductive ends for sensing the impedance of tissue about the tip 103 of the shaft 102. An impedance sensor 104 (which includes electrical circuitry that senses impedance) electrically connected to the conductive ends senses the electrical impedance. Electrical devices and circuits that sense the electrical impedance between two points, e.g., in a material or in a circuit, are known in the art. An electrically controlled driver 106 drives the shaft 102 to penetrate the skin of the patient and tissue under it, which can be referred to as the "substrate" of penetration. The driver 106 is controlled by a processor 108, which stops the driver when the impedance sensor 104 senses an impedance change indicating the desired penetration has been achieved.

For illustration, FIG. 2A shows an embodiment of a portion of a hypodermic needle 110 that can be used in the present invention, e.g., as the shaft 102 in the apparatus 100. FIG. 2A is a sectional view along the axis of the hypodermic needle 110 and FIG. 2B shows a cross section of the hypodermic needle 110. The hypodermic needle 110 includes a stiff shaft body 112 halting a sharp tip 114 at the distal end 115 for penetration into tissue. The shaft body 112 has a stiff, electrically non-conductive (e.g., polymeric, such as polyimide) tubing 116 with a central lumen 118 at the axis of the tubing 116. An electrically conductive (e.g., metallic tungsten) wire 120 located at the approximate axis of the tubing 116 extends from the sharp tip 114 proximally. The tungsten wire 120 has a distal conductive end 123 proximate to the distal end 115. As used herein, the term "distal" refers to the direction towards the object (e.g. the patient's skin) when the needle is about to penetrate the object and the term "proximal" refers to the direction opposite to that of "distal," therefore away from the object. An electrically conductive coating 122 (e.g., chrome/gold plated coating) is disposed on the outer surface of the nonconductive tubing 116 and has conductive end 125 at the tip 114. An adhesive 124 (see FIG. 2A), preferably electrically conductive, such as a silver epoxy, is used to attach the distal end of the electrically conductive wire 120 to the distal end 115 of the hypodermic needle 110.

Furthermore, if desired, a chamber or reservoir can be connected to the lumen 118 for collection of the fluid that may conduct through the lumen. This chamber or reservoir can be a nonconductive bag, a syringe, other tubings connected to the lumen, and the like.

Such a hypodermic needle can be made by, for example, electroplating a polyimide tubing to deposit the electrically conductive coating on the polyimide tubing and inserting, for example, a tungsten wire into the polyimide tubing and affixing an end of the wire to the distal end of the hypodermic needle with a silver epoxy. The distal end can be sharpened after all the conductive materials are in place. The proximal end of the electrically conductive wire 120 and the proximal end of the electrically conductive coating 122 can be connected to the impedance sensor 104 in the apparatus 100, or other similar equipment for sensing the penetration depth of the hypodermic needle 110. Other suitable materials for making the electrically conductive coating include, for example, silver, nickel, platinum, titanium, and tungsten. Materials suitable for making the electrically conductive wire include, for example, silver, nickel, platinum, titanium, gold, copper, aluminum, and tungsten.

In another embodiment, as shown in FIG. 3, a solid needle assembly 126 can be made by filling the lumen 127 of a hollow nonconductive needle 128 with a conductive material 130 and coating on the non-conductive needle with a metallic coating 132. The resultant elongated structure can be modified to produce a sharp tip. Alternatively, a non-conductive material can be coated on a stiff metallic wire and then an outer coat of conductive metal can be coated on the non-conductive material to form a solid needle. Such a needle will have a structure similar to that shown in FIG. 3, which shows a cross section of the shaft.

To further stiffen a needle shaft for penetration, the needle having conductors leading to the distal end can be further coated with a material that provides additional rigidity. Many hard materials, such as metals or alloys are known in the art. An example of a material suitable for providing such additional rigidity is titanium nitride.

FIG. 4 shows another embodiment of a hypodermic needle of the present invention. In the hypodermic needle 134 shown in FIG. 4, an inner electrically conductive tubing 136 with a lumen 138 has a coating of a non-conductive material 140 electrically insulating the inner tubing 136 from an electrically conductive coating 142 that is more remote from the axis. This hypodermic needle 134 can be made by coating, e.g., a steel needle with a non-conductive material and then sputtering a metallic coating on the electrically non-conductive material and fewer electroplating to form the outer electrically conductive coating 142.

Figure 5A:
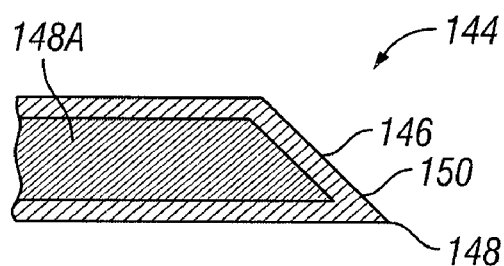
FIGS. 5A and 5B show a lancet of the present invention.
Figure 5B:
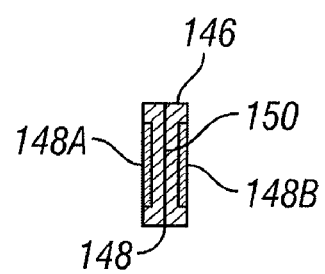

FIGS. 5A (a side view) and 5B (a front view) show yet another embodiment in which a shaft suitable for inserting into the skin of a patient has conductors for sensing impedance of the tissue surrounding the tip of the shaft. The shaft 144 has a rectangular cross section (see the front view of FIG. 5B) and has a central part 146 made of a stiff non-conductive material extending lengthwise along the shaft 144 sandwiched between two conductors 148A and 148B. The central part has a sharp tip 148 leading into a sharp edge 150 for cutting into a skin. Such a shaft can be used as a lancet for cutting a wound in the skin to yield blood.

Mechanisms for Driving the Shaft

A wide variety of drivers can be used to drive the shaft (including needles, lancets, blades) of the present invention. Such drivers can be electrically controlled such that when the desired depth has been achieved, the driver can be stopped, preferably, automatically. In this way, the depth of penetration can be optimized so that minimal penetration is used to achieve the desired result, such as drawing blood from a patient with the infliction of a minimal amount of pain and wound size. Examples of mechanisms that can be used for the driver include pneumatic, electromechanical, and piezoelectric mechanisms.

Figure 6A:
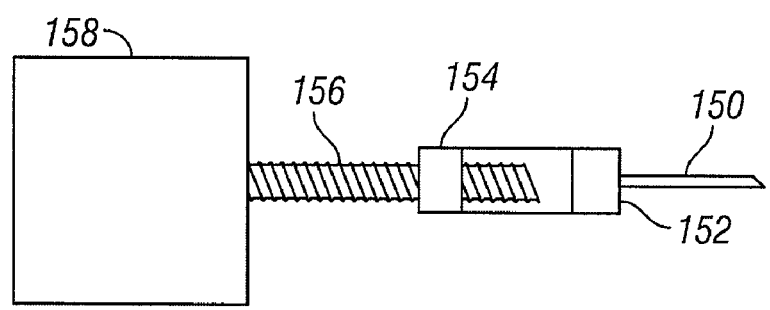
FIGS. 6A and 6B show apparatuses including an embodiment of a driver for driving a shaft according to the present invention.

FIG. 6A shows an apparatus with a driver for driving a shaft continually with a threaded mechanism. In the embodiment of FIG. 6A, the shaft 150 is affixed to a base 152 rigidly linked to a sleeve 154, which mates with a threaded rod 156. The threads of the sleeve 154 are so engaged with the threads of the threaded rod 156 such that the rotation of the threaded rod 156 will move the sleeve 154 along the threaded rod 156 axially. Therefore, a motor 158 that drives the rotation of threaded rod 156 in a direction (e.g. clockwise rotation) will drive the forward motion of the shaft 150 in the distal direction. Stopping the motor 158 will stop the forward advance of the shaft 150. Holding the motor 158 at a fixed position relative to the object to be penetrate and controlling the motor will control the depth of penetration of the shaft 150. Furthermore, the motor 158 can be driven to advance incrementally in an intermittent, stepwise fashion. If desired, the motor 158 can be operated to rotate in two directions to provide both forward and backward motion for advancing and withdrawing the shaft 150.

Figure 6B:
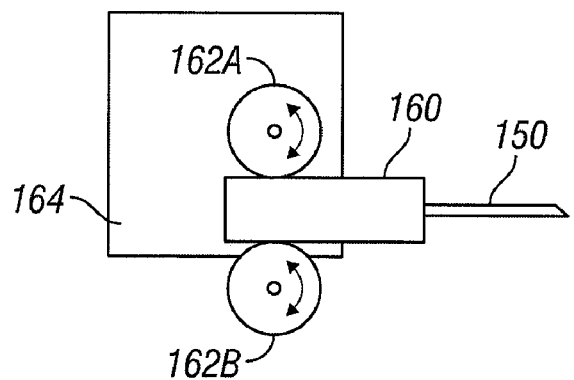

FIG. 6B illustrates another embodiment in which the shaft can be driven to advance continually. In this embodiment, a shaft 150 (e.g., a needle) is affixed to a base 160. The base 160 (and therefore the shaft 150) is driven to move in the forward, i.e., distal, direction by a rotor 162A that engages the base 160 on the side such that rotating the rotor 162A will move the base 160 and shaft 150 distally. The rotor 162A is driven by the a motor 164. Another rotor 162B engages the base 160 on a side opposite that of the rotor 162A for support. Either rotor 162A or rotor 162B can be an idler rotor. The rotors 162A and 162B can engage the base 160 by means of gears or by friction.

Figure 7A:
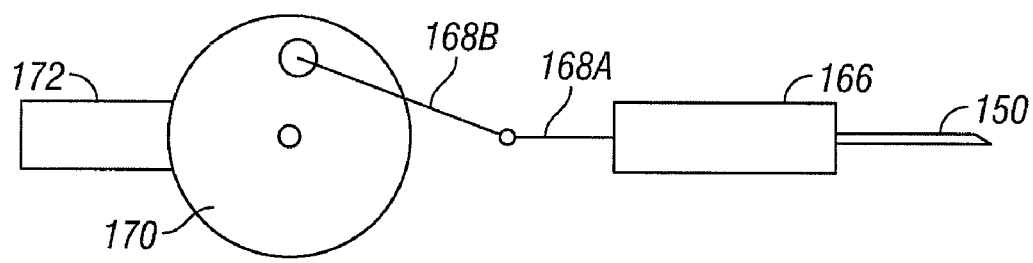
FIG. 7A shows an apparatus including an embodiment of a driver for driving a shaft.

FIG. 7A shows an embodiment of a shaft-penetration apparatus of the present invention with reciprocative action for inserting the shaft into a body. A shaft 150 is affixed to a link 166 actuated by linking arms 168A, 168B. The linking arms 168A and 168B are pivotably connected to each other. The linking arm 168B is pivotably connected off center to the rotor 170, which in turn is driven by motor 172. Thus, the rotation of the rotor 170 results in a back and forth reciprocative movement of the linking arms 168A, 168B, which is translated to the shaft 150. In addition, the whole system can be move steadily forward distally to advance the shaft 150 distally.

Figure 7B:
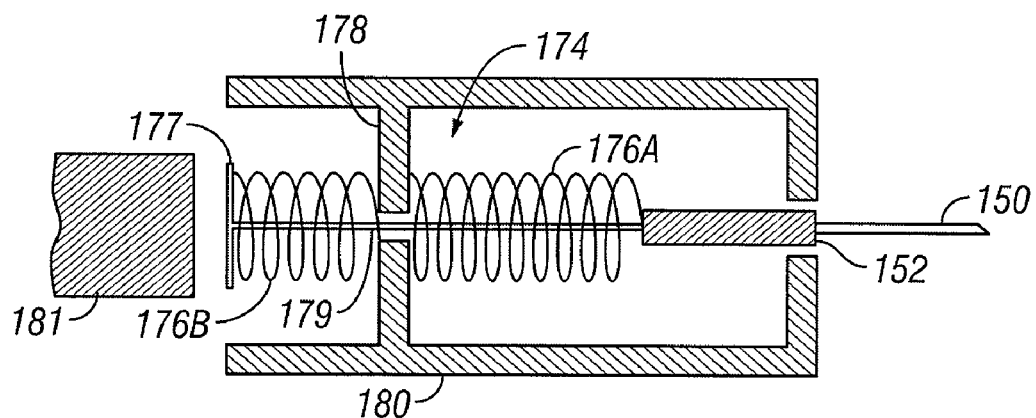
FIG. 7B shows an apparatus including a portion of an embodiment of a driver for driving a shaft.

FIG. 7B shows an embodiment of a spring mechanism 174 that can be used, e.g., as the link 166. The shaft 150, supported on a base 152 is held by the spring mechanism 174, which consists of a primary spring coil 176A and a secondary spring coil 176B. The primary spring coil 176A and secondary spring coil 176B are each held at one end by a ledge 178 of a housing 180, which houses the spring coils and part of the base 152. An end disk 177 is disposed at the proximal end of the spring coils 176A, 176B and affixed to the base 152 by a rigid rod 179 that extends through the axis of the spring coils 176A, 176B. A hammer 181 (shown in portion) can be used to impact the end disk 177, which drives the shaft 150 forward by means of rigid rod 179. After the impact, the springs 176A and 176B can move the shaft backward. It is noted that one of the springs 176A and 176B is optional and an alternative is to use only one of them.

Figure 8:
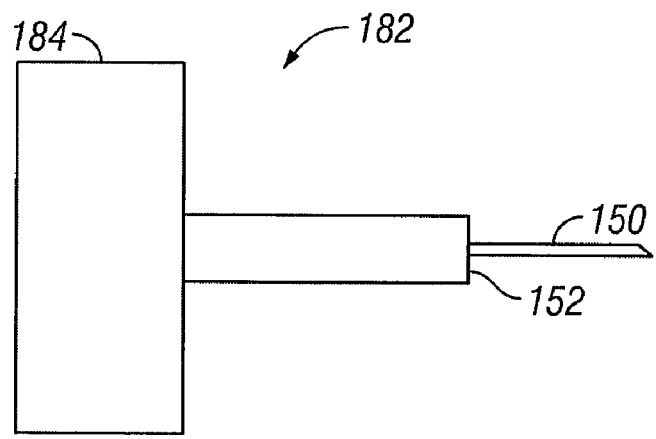
FIG. 8 shows an apparatus including a portion of a piezoelectric driver for driving a shaft.

FIG. 8 shows an example of a piezoelectric driver 182 for producing a reciprocative motion to drive a shaft for penetration. As in the aforementioned embodiments, a shaft 150 is affixed to a base 152, which is attached to a piezoelectric vibrator 184. When energized electrically, the piezoelectric vibrator 184 will vibrate to move the base 152 and the shaft 150 in a forward-backward motion. This whole vibrating driver system 182 can be advanced forward. Technique for making and using piezoelectric vibrators are known in the art and can be easily adopted for driving a shaft based on the present disclosure.

Figure 9:
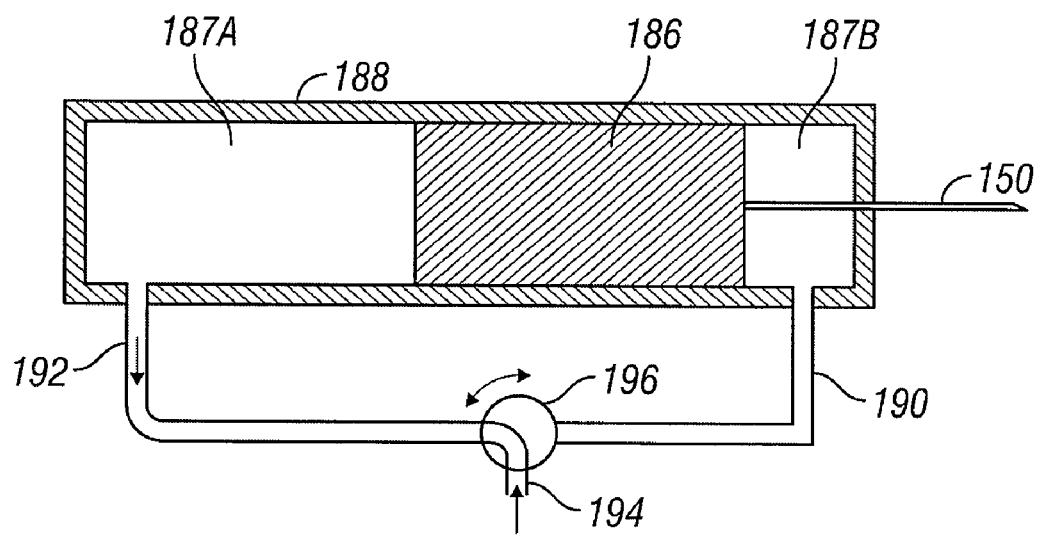
FIG. 9 shows an apparatus including a portion of a fluid-driven driver for driving a shaft.

FIG. 9 shows a fluid mechanism for driving a reciprocative motion for driving a shaft. Here, a shaft 150 is attached to a piston 186 that is allowed to slide inside a chamber (shown in the figure including the chamber 187A, chamber 187B and the volume occupied by the piston 186) in a piston housing 188. A distal fluid conduit 190 distal to the piston 186 allows a fluid to enter the chamber 187B to drive the piston proximally, i.e., in a direction opposite to the distal direction. At the same time, preferably, a proximal fluid conduit inlet 192 proximal to the piston 186 can allow fluid to escape to facilitate the movement of the piston without building excessive pressure in the chamber 187A. Conversely, the proximal fluid conduit 192 can allow fluid to enter the chamber 187A to drive the piston distally while the distal fluid conduit 190 allows fluid to escape. A common fluid inlet conduit 194, connected to a multi-way valve 196 (e.g., three-way valve) can allow fluid to enter the proximal fluid conduit 192 or distal fluid conduit 190. Alternately admitting fluid into the chamber 187 proximal and distal to the piston while at the same time releasing fluid on the opposite side of the chamber will result in a reciprocative motion. To effect a progressive advance of the shaft 150 at the distal direction, over time, more fluid can enter the proximal conduit 192 than the distal fluid conduit 190. Optionally, one or both of the chambers 187A and 187B can be kept close to the environmental pressure so as to not put too much stress on the structure of the mechanism. Alternatively, the whole mechanism shown in FIG. 9 can be advanced while it is reciprocatively moving. A gas or a liquid can be used as the fluid for entering the chamber 187 to drive the progressive movement of the shaft 150.

The present invention can also find application in which the shaft advances in a sawing action, as that described in a copending application (Attorney Docket Number 10971004-1, Inventors: Ganapati Mauze, et al., entitled "APPARATUS AND METHOD FOR INCISING") submitted on the same day and assigned to the same assignee as the present application. Said copending application is incorporated by reference in its entirety herein. An example of such all apparatus has an elongated structure for conducting blood with an outer tube and an inner tube. The tubes associated with each other in concentric, close proximity with low friction between them so that one can slide on the other freely. The distal ends of the tubes each has a circular sharp cutting edge. The tubes are driven to move longitudinally reciprocatively such that alternately the sharp ring-shaped end of the outer tube is more distal than the end of the inner tube and the sharp ring-shaped end of the inner tube is more distal than the end of the outer tube. In this way, the elongated structure can penetrate the tissue by a sawing action by the two tubes.

Figure 10:
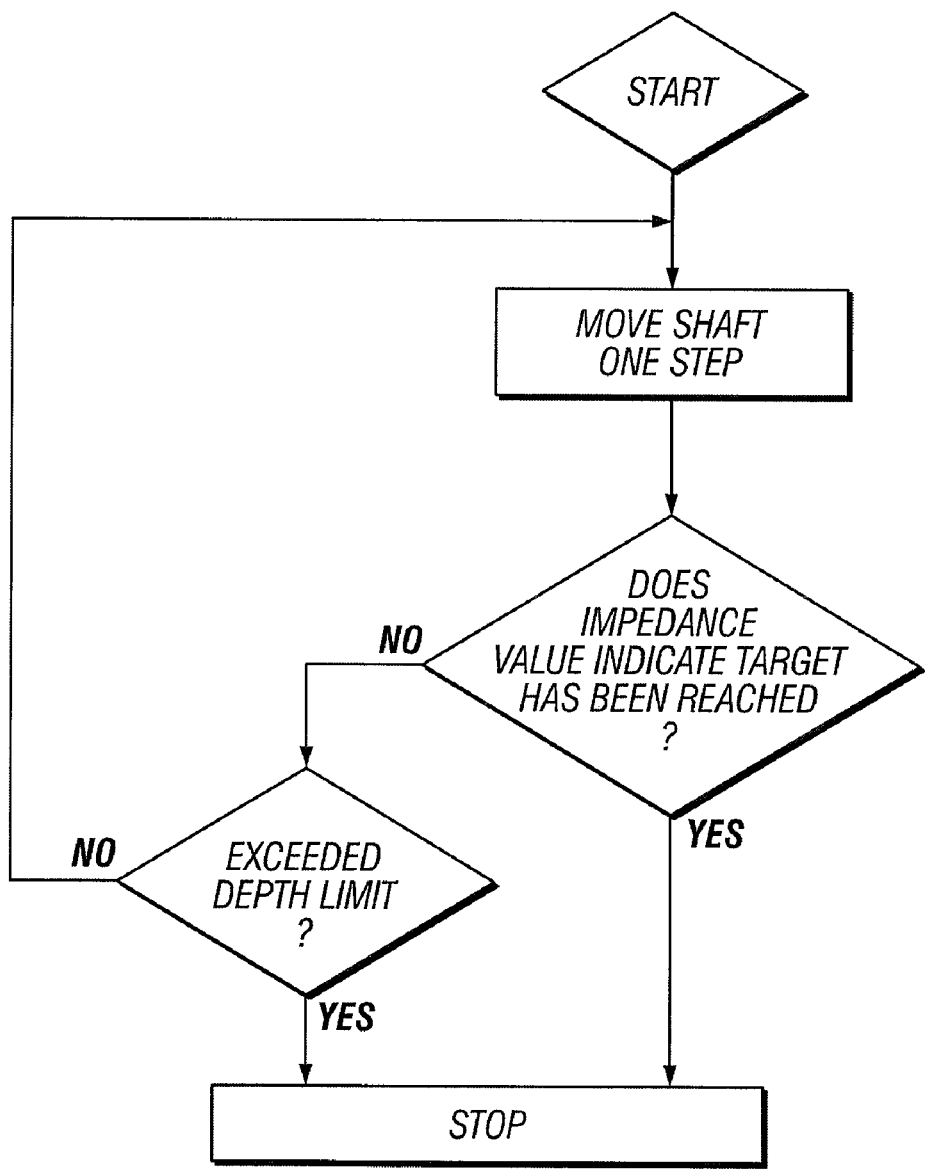
FIG. 10 shows a flow diagram for an algorithm for controlling the driver for driving a shaft according to the present invention.

The driving mechanism for driving the shaft (e.g., needle, lancet, and the like) of the present invention can be controlled by feedback electronics circuits that inhibit further shaft penetration once a proper depth of fluid material has been sensed. Typically, such a control system would be placed in the processor shown in FIG. 1. A control algorithm for such a control-system is illustrated by an exemplary flow diagram shown in FIG. 10. In this algorithm, once initiated, the driver will move the shaft one step at a time to advance an incremental distance until either the impedance measured indicate that the shaft has reach the target area (e.g. blood in capillary bed by a needle penetrating skin) or until the predetermined depth of penetration has been reached, at which point the driver will be stopped by the control circuitry. Whether the proper depth has been reached by the shaft can be determined by the magnitude of the change in impedance or the magnitude of the impedance itself. The selection of impedance values or jump values can be done by one skilled in the art. A processor can be provided external to the object that is being penetrated by the shaft for gathering and processing the impedance information to determine whether the desired depth has been achieved, as well as to control the movement of the shaft. Electrical devices and electrical circuits for processing information, controlling drivers, as well as those for sensing electrical impedance are known in the art. Such devices and circuits could include computers or microprocessors.

To use the apparatus of the present for the optimal benefit, preferably, the change in impedance with the depth of penetration is determined experimentally. After a few times of sampling, the apparatus can be adjusted to set the depth of insertion in relation to impedance changes to fit the particular preferences (e.g., penetration depth and sample volume) of that individual. Another way would be to obtain impedance data versus depth specifically for an individual patient and, after taking data from a plurality of blood samples, use the resultant data for setting the depth of penetration for future blood samples.

Although the preferred embodiment of the present invention has been described and illustrated in detail, it is to be understood that a person skilled in the art can make modifications within the scope of the invention. For example, it is understood that the present invention can be applied in a wide variety of medical or nonmedical areas, e.g., drilling in the ground for water, gas, petroleum, etc.

What is claimed is:

1. A tissue penetrating device for sampling body fluid from a patient and for use with a penetrating member, the device comprising:
    an electrical driver coupled to provide force that moves said penetrating member along a path into the tissue;
    a sensing device for use in controlling motion of the penetrating member to penetrate the skin of the patient to a desired depth of penetration that is sufficient to create a wound from which blood flows from the wound and into an interior of the tissue penetrating device for blood analysis without flowing through the penetrating member for blood analysis with reduced patient discomfort from the creation of the wound;
    a controller electrically coupled to the electrical driver and configured to receive a signal from the sensing device to control the electrical driver and a motion of the penetrating member;
    an electronic feedback loop circuit in electrical communication with the sensing device, the electrical driver and the sensing device configured to control a motion of the penetrating member; and
    wherein the electrical driver is used to stop the penetrating member in the tissue.

2. The device of claim 1 wherein the electronic feedback loop circuit in electrical communication with the sensing device and the controller inhibits penetrating member penetration once a penetration depth of the penetrating member has been sensed by the sensing device.

3. The device of claim 1 wherein the electrical driver includes a motor.

4. The device of claim 1 wherein the controller includes a microprocessor.

5. The device of claim 1 wherein the controller has logic for directing the electrical driver to provide force to drive the penetrating member into tissue and to provide force to withdraw the penetrating member from tissue.

6. The device of claim 1 wherein the penetrating member comprises a non-hollow, elongate member.

7. The device of claim 1 wherein the controller has logic for directing the electrical driver to provide force to drive the penetrating member into tissue and to provide force to withdraw the penetrating member from tissue.

8. A method of lancing the tissue of a patient using a tissue penetrating device, comprising:
    providing a penetrating member device comprising, an electrical driver coupled to provide force to a penetrating member;
    activating the electrical driver;
    driving the penetrating member into the tissue of a patient, wherein the electrical driver provides force to move said penetrating member into the tissue;
    using a controller electrically coupled to the electrical driver to control a motion of the penetrating member;
    sensing the depth of penetration of the penetrating member after the penetrating member has been driven into the patient's tissue with the sensing device and controlling the activation of the electrical driver with the controller based on the depth of penetration of the penetrating member;
    using the electrical driver to stop the penetrating member in the tissue, and
    using the electrical driver to withdraw the penetrating member from the tissue.

9. The method of claim 8 further comprising:
    obtaining the body fluid sample, wherein the sample is obtained only by removing the penetrating member from the tissue.

10. The method of claim 8 wherein the penetrating member comprises a non-hollow, elongate member.

11. A method of sampling blood from a patient, the method comprising:
    providing a tissue penetrating device that includes, an electrical driver coupled to a penetrating member, the electrical driver for providing drive force, a controller electrically coupled to the electrical driver, and
    an electronic feedback loop circuit in electrical communication with a sensing device, the electrical driver and the sensing device configured to control a motion of the penetrating member, wherein motion of the penetrating member results in motion of at least one component of the sensing device relative to a housing;
    activating the electrical driver;
    driving the penetrating member through the skin surface of a patient into the patient's tissue;
    sensing a depth of penetration of the penetrating member after the penetrating member has been driven into the patient's tissue; and
    controlling activation of the electrical driver in response to a depth of penetration of the penetrating member determined with the sensing device member to penetrate the skin of the patient to a desired depth of penetration that is sufficient to create a wound patient's tissue;
    sensing a depth of penetration of the penetrating member after the penetrating member has been driven into the patient's tissue; and controlling activation of the electrical driver in response to a depth of penetration of the penetrating member determined with the sensing device member to penetrate the skin of the patient to a desired depth of penetration that is sufficient to create a wound from which blood flows from the wound without flowing through the penetrating member and into an interior of the tissue penetrating device for blood analysis with reduced patient discomfort from the creation of the wound;

wherein the electrical drive is used to stop the penetrating member in the tissue.

12. The method of claim 11 further comprising:
obtaining the body fluid sample, wherein the sample is obtained only by removing the penetrating member from the tissue.

13. The method of claim 11 wherein the penetrating member comprises a non-hollow, elongate member.

14. The method of claim 1 further comprising using the electrical driver to stop the penetrating member in the tissue.

15. The method of claim 11 further comprising using the electrical driver to withdraw the penetrating member from the tissue.

* * * * *